United States Patent [19]

Allington

[11] Patent Number: 5,336,383
[45] Date of Patent: Aug. 9, 1994

[54] PULSED FIELD GEL ELECTROPHORESIS OF LARGE DNA

[75] Inventor: Robert W. Allington, Lincoln, Nebr.
[73] Assignee: Isco, Inc., Lincoln, Nebr.
[21] Appl. No.: 495,899
[22] Filed: Mar. 15, 1990

Related U.S. Application Data

[63] Continuation-in-part of Ser. No. 348,679, May 5, 1989, Pat. No. 5,135,628.

[51] Int. Cl.$^5$ .................. G01N 27/26; G01N 27/447
[52] U.S. Cl. ........................... 204/182.8; 204/299 R
[58] Field of Search .................. 204/299 R, 182.8

[56] References Cited

FOREIGN PATENT DOCUMENTS 359589 3/1990 European Pat. Off. .

OTHER PUBLICATIONS

David C. Schwartz & Michael Koval "Conformational dynamics of individual DNA molecules during gel electrophoresis" Nature vol. 338 (Apr. 6, 1989) pp. 520–522.

Primary Examiner—T. Tung
Assistant Examiner—John S. Starsiak, Jr.
Attorney, Agent, or Firm—Vincent L. Carney

[57] ABSTRACT

To separate high-molecular DNA strands, an electrophoresis system includes first means for changing the direction of an electric field within an electrophoresis separating unit at a first frequency having a period of no more than 20 seconds and second means for changing the electric field in another manner at a second frequency at least twice as high as the said first frequency. In one embodiment, the field strength in the direction of overall migration is selected so that, considering the DNA size and gel density, the leading segment of DNA to the first corner is sufficiently small so that excess friction forces due to bunching does not cause excessive band spreading. The field strength is selected so that the electric field is reduced until the changing of the electric field at the second frequency keeps the bunching effect to a sufficiently low level to not seriously interfere with the separation.

11 Claims, 10 Drawing Sheets

PULSED FIELD GEL ELECTROPHORESIS OF LARGE DNA

RELATED CASES

This application is a continuation-in-part of an application entitled "Pulsed Field Gel Electrophoresis of Large DNA", Ser. No. 348,679 now U.S. Pat. No. 5,135,628; filed May 5, 1989, in the name of Robert W. Ailington.

BACKGROUND OF THE INVENTION

This invention relates to pulsed field gel electrophoresis of large DNA.

In the process of separating DNA molecules by electrophoresis, an electric field is applied across a gel to separate DNA molecules as they are moved by the field through the gel.

It is known to use the characteristics of the field established across the gel to control the electrophoresis for maximum separation. The fractionation of different molecular weight DNAs is presumably due to the sieving effect of the agarose gel matrix rather than differing electrophoresis mobilities of the DNAs as found in a free (completely liquid) medium.

In one prior art technique of electrophoresis that has been used for separating DNA, a static, unidirectional electric field is applied to a DNA sample resulting in the migration of the DNA molecules through the agarose. This technique is referred to as continuous field electrophoresis. Continuous field electrophoresis easily separates DNA molecules of size up to about 20,000 base pairs.

Continuous field electrophoresis has a disadvantage in that for DNA molecules of sizes above approximately 20,000 base pairs, separation becomes more difficult because the migration rate becomes independent of molecular size except at very low field voltages. At very low field voltages, separations take a long time. Usually, the practical upper limit is reached at a separation time of about two wee k s because DNA degrades at temperatures suitable for electrophoresis at times longer than this. This long time period is believed to be due to the extreme difficulty of totally eliminating minute amounts of nuclease from the system.

Several techniques are known to be successful in resolving larger chromosome fragments. Some of these techniques are successful in resolving chromosome fragments larger than 1 megabase in agarose gels . These techniques are different forms of pulsed field gel electrophoresis (PFGE) which is the resolution of large DNA molecules by periodically changing the electric field pattern during electrophoresis to produce DNA migration direction changes. These direction changes typically vary from close to 90 degrees to greater than 120 degrees. Sometimes these direction changes are curved loops, such as a sequence of curved segments with individual angles of arc. At other times, they are a zigzag path with concentrated angle changes of direction at the corners. The changes in field pattern reorient the DNA molecules and the separating medium, thus improving DNA separation.

In the prior art PFGE techniques, the pulse lengths relating to changing the field pattern are of sufficiently long duration to change the gross configuration of the DNA, being longer than one second in duration for the separation of large DNA. The changes in gross configuration are affected by the pulse duration and changes in direction and may vary from realigning direction of a substantially straight elongated strand to creating hooks or staircase-shaped strands.

Each of the prior art pulsed field techniques has the disadvantage of using a time duration for changing the field pattern that is in the order of a second or longer for separating large DNAs.

With pulsed field gel electrophoresis (PFGE) as usually practiced, it is easy to separate large DNA of size up to one million base pairs. Above this size it it becomes progressively more difficult. In order to get clear separations of larger DNA, the field voltage must be reduced and the angle-switching time increased. For example, the largest chromosome of the yeast *Saccharomyces cerevisiae* (YPH 80) about 1.5 megabase pairs, can be resolved in 15 hours with a field switching time of 120 seconds per direction and at a field voltage of 6 volts per centimeter. It is believed that this is an optimum separation. However, the *S. pombe* chromosomes of 3, 4.5 and 5.7 megabase pair require a switching time of 30 minutes per direction and a field of 115 volts per centimeter. The separating time is 3 to 6 days. It is believed that this is also an optimum separation. If the field voltage is raised in an attempt to get a faster separation, the DNA does indeed move faster but it smears out so that the bands overlap and no separation is discernible.

In the past, orthogonal pulses of duration too short to allow change in DNA configuration to take place were expected to appear as a vector sum, and be generally useless for separating DNA. This lack of separating effect was predicted in Schwartz, D.C. (1985) "Giga-Dalton Sized DNA Molecules ," p. 84, doctoral dissertation, Columbia University (University Microfilms International).

The prior art is deficient in some respects in providing adequate explanations of why pulsed field techniques provide the result that has been observed. As part of the development of the invention, a novel explanation has been developed.

According to this novel explanation, the limitations of ordinary pulsed field gel electrophoresis (PFGE) for separating very large DNA occurs because of the electric field and time dependent forking, tumbling and bunching motion of DNA in gel. These effects have been reported and recorded on videotape cited by Smith, S.B., Aldridge, P.K., and Calles, J.B. (1989); *Science* 243 203–206. The videotape shows actual motion of DNA in constant and varying electric fields: Smith, et al (1989); "Observation of Individual DNA Molecules Undergoing Gel Electrophoresis"; University of Washington Instructional Media Services, Source L66-79-90, University of Washington, Seattle, Wash. 98195.

DNA is negatively charged and therefore a straight length of DNA has a positive counterion sheath around it when in an aqueous buffer solution. The positive ion in buffer solutions used for DNA electrophoresis is Tris. Tris is selected as the positive ion because it does not bind to the DNA. A consequence of this is that Tris ions comprising the counterion sheath are free to move along the length of the DNA in response to electrical and thermal diffusion forces.

If the DNA molecule is located in an electric field parallel to its length, it starts to migrate straight toward the positive electrode because it has a negative charge. However, the counterion sheath has a positive charge and therefore tends to be repelled from the positive electrode. The counterion sheath does not leave the DNA because this would expose the negative charge of the DNA thus bringing the counter ion sheath back. However, the centroid of the counterion sheath shifts toward the trailing edge of the molecule.

Because the centroid of the counterion sheath shifts toward the trailing edge of the molecule, the trailing end of the molecule is surrounded with more positive charges than the leading end. The trailing end of the molecule is immersed within this concentrated charge and is surrounded by it. The leading edge of the molecule is outside of the concentrated charge area and "sees" the concentrated charge behind it. This decreases the net electric field on the leading edge of the molecule to a larger extent but decreases the net electric field on the trailing end of the molecule to a lesser extent.

Because the net electric field on the trailing edge is decreased less than the net electric field on the leading edge, the trailing end of the molecule tends to migrate faster than the leading end of the molecule, causing the bunching phenomenon reported by Smith and others. This effect may be aggravated in pulsed field gel electrophoresis when the DNA is long enough to be completely engaged in a previous corner-turning at the time the next corner turning starts. This is because the trailing, concentrated counterion sheath will be particularly concentrated at a previous sharp corner in the DNA where there are two continuous segments of it in close proximity.

When the DNA molecule bunches up and is no longer linear, its counterion polarizability decreases because of the decrease in effective length of the DNA. The DNA becomes more isotropic; more compact than elongated. The positive counterion sheath then becomes more isotropic, encouraging a leading end of the DNA to propagate out of the bunched up DNA, and eventually pulling out the bunched DNA into a more or less straight length of DNA.

As before, the counterion sheath becomes more concentrated at the trailing end of the length of DNA than the leading end, but because of the finite relaxation time of the counterion sheath it takes a while, such as 30 seconds, for it to do so. When the counterion sheath becomes sufficiently anisotropic, the DNA bunches up again and the cycle repeats. Under some circumstances, this phenomenon does not repeat at very regular, clock-like, intervals, and therefore, each DNA molecule can accumulate an error in its overall velocity compared to the average of the overall velocities of all the DNA of that species being separated.

This causes the observed band broadening and a smeared "nonseparation" if the effect is bad enough. Higher electric fields and longer free leading lengths of DNA cause more profound bunching problems. The foregoing can explain the faster separations possible at higher buffer concentrations than at lower buffer concentrations, because at higher buffer concentrations, counterions are known to form a thinner layer at the surface of a charged molecule. A thinner trailing counterion layer exerts less bunching influence at the leading end of the DNA.

Counterion sheath polarization also can explain snap-back of the leading end of DNA undergoing electrophoretic migration as the field is removed. This snap-back is shown in the Smith, et al. videotape. The effect may arise because the internal field from the displaced counterion sheath pulls back the leading end of the DNA before the counterion sheath anisotropy has time to relax upon external field removal. Smith attributes this effect to an "entropic spring" effect as the DNA pulls back into a random coil upon removal of the field. However, it is hard to see how this could cause rapid movement, since movement into a random coil is inhibited because the DNA is threaded through the pores of the gel.

The tendency toward bunching, combined with frictional forces, explains why it is more difficult to separate 6 megabase DNA than it is to separate 1 megabase DNA with ordinary pulsed field electrophoresis. In pulsed field gel electrophoresis, DNA is forced to turn successive sharp corners. The hydrodynamic or boundary friction drag retards the DNA molecule as it goes around each corner along its length, thus cumulatively tensioning the segment of the molecule behind the leading corner. This should be the case regardless of whether boundary friction or hydrodynamic friction is dominant at a corner.

Corner turning friction is believed to account for much of the differential mobilities of different lengths of DNA. The average number of corners turned per unit distance of migration is directly proportional to the length of the molecule. The frictional force increases as a rapid function of the sum of the number of corners turned. This is because, at the front-most or leading corner, frictional drag from the following corners along the length of the DNA adds additional tension which either increases boundary friction force at the leading corner or decreases the thickness of the hydrodynamic layer between the DNA and the gel strands defining the corner. A thinner hydrodynamic layer results in higher viscous friction forces between the gel strand and the DNA. The retardation force due to the corners turned by the DNA is an exponential function of the summation of the angles of all the corners. This follows from basic engineering theory relating to ropes on capstans, belts on pulleys, etc. Tensioning of the DNA around the leading corner arises from the pull of the electric field on the segment of DNA ahead of the leading corner, working with frictional drag on the segment of DNA behind the leading corner. If the turn angle at the leading corner exceeds 90 degrees, a component of the electric field will exert a reverse pull on the DNA segment behind the corner, adding to the tensioning at the corner. This can account for the fact that corner angles greater than 90 degrees (typically 120 degrees) work better than angles of 90 degress or less with pulsed field electrophoresis. It can be seen that alternate corners do not have this field tensioning effect at any one time. However, when the field makes one of its periodic direction changes, the corners which previously had no tensioning due to field effects become tensioned due to field effects. Conversely, corners which previously were tensioned at least partly due to field effects lose this component of tensioning. Since all corners have the same tensioning mechanisms, they can be considered as a group.

The reason that ordinary pulsed field electrophoresis can easily separate DNA of size greater than 20 kilobase pairs but less than one megabase pairs is that the leading end of a migrating DNA molecule is closer to the leading (most recently) turned corner than it is to the other end of its own length. Since the polarizability of the counterion sheath of a linear molecule is proportional to the cube of its length in the direction along the electric field, the effective polarizability of the free or leading length of the molecule is only the length from the leading end to the location of the most recent corner turning. With ordinary pulsed field electrophoresis, this should allow the use of higher electric fields and therefore faster migration rates compared to conventional constant field electrophoresis, with less serious problems with the bunching problem described previously.

The foregoing explanation is consistant with the increasing difficulty that is observed when trying to separate DNA molecules progressively larger than 1 megabase pairs in length with ordinary pulsed field electrophoresis.

SUMMARY OF THE INVENTION

Accordingly, it is an object of the invention to provide a novel pulsed field gel electrophoresis (PFGE) technique for separating large DNA with increased rapidity.

It is a further object of the invention to provide a novel pulsed field electrophoresis apparatus for separating large DNA more rapidly than heretofore.

It is a still further object of the invention to provide a novel pulsed field electrophoresis apparatus for separating DNA larger in size than heretofore possible.

It is a still further object of the invention to provide a novel pulsed field DNA electrophoresis technique or apparatus incorporating interruption pulses which occur more rapidly than the low-frequency migration direction changes corresponding to the usual pulsed field electrophoresis, and which stabilize the motion of the DNA molecules.

It is a still further object of the invention to provide a novel pulsed field DNA electrophoresis technique or apparatus that incorporates short-duration changes in the direction or magnitude of the electric field, which occur more rapidly than the low frequency DNA migration direction changes corresponding to the usual technique of pulsed field DNA electrophoresis, and which stabilize the motion of the DNA molecules.

It is a still further object of the invention to provide a novel pulsed field DNA electrophoresis technique using a field switching angle which is easily changeable by varying the time duration ratio of a perpendicular and parallel field at a frequency higher than that corresponding to the time for DNA to change its gross configuration under the influence of the field.

It is a still further object of the invention is to provide a novel pulsed field DNA electrophoresis apparatus that: (1) uses a field switching angle which is easily changeable by varying the time duration ratio of a perpendicular and parallel field at a frequency higher than that corresponding to the time for DNA to change its gross configuration under the influence of the field; and (2) does not require an external computer or a matrix of matched or expensive circuits.

It is a still further object of the invention to provide an apparatus which improves the interaction between the DNA being separated and the gel matrix to produce faster separation of very large DNA.

It is a still further object of the invention to provide a low cost, versatile PFGE system for routine laboratory use which permits electric field force, electric field angle and interruption pulse duration to be set to preferred parameters.

It is a still further object of the invention to provide novel electrophoresis apparatuses and techniques for resolving DNA molecules greater than 1,000 kb. and result in straight, unbent lanes.

It is a still further object of the invention to provide novel electrophoresis apparatuses and techniques that that provide repeated successive orthogonal field pulsing at a first angle perpendicular to and on a first side of an overall direction of migration of the DNA and at a later time reversing to the opposite perpendicular angle on the opposite side of the overall direction of migration.

It is an object of the invention to provide a novel method of separating proteins including DNA by electrophoresis in which the interruption frequency, direction and magnitude of the field are selected in accordance with the size of the molecules being resolved to minimize tumbling, hooking to reduce compaction or bunching at matrix elements for still larger molecules.

It is a still further object of the invention to provide a technique for electrophoresis of large DNA molecules in which the characteristics of the field such as strength, frequency and/or direction of field are selected to avoid frictional drag that overcomes migration speed from a higher potential caused by bunching of the leading segment of the DNA up to the first corner.

It is an object of the invention to provide a technique for electrophoresis in which the leading segment of the DNA is maintained sufficiently linear for efficient separation of DNA by size.

It is a still further object of the invention to provide a novel technique for electrophoresis of large DNA molecules in which the benefit of increased force from high field strength is made more useful by decreasing the bunching caused by high field strength.

It is a still further object of the invention to provide a technique for determining good field strength values and pulse characteristics for separation of large molecules by electrophoreses.

In accordance with the above and further objects of the invention, an electrophoresis system includes first means for changing the direction of an electric field within an electrophoresis separating unit at a first frequency and second means for changing the electric field in another manner at a second frequency at least twice as high as the said first frequency. The electrophoresis system is operated to cause improved separation of large molecules by reducing hooking, tumbling and especially bunching which is changing to larger diameter because of compaction of large molecules and principally compaction of the molecules at the leading segment ahead of the first bend for still larger molecules.

In one embodiment, the second changes are changes in the magnitude of the electric field and or changes in the direction of the electric field. The first changing means changes the angle of the field to impart a zigzag path to DNA molecules being separated. In one embodiment, the field strength in the direction of overall migration is selected so that, considering the DNA size and gel density, the leading segment of DNA to the first corner is sufficiently small so that excess friction forces due to bunching does not cause excessive band spreading. The field strength is selected so that the electric field is reduced until the changing of the electric field at the second frequency keeps the bunching effect to a sufficiently low level to not seriously interfere with the separation.

For effective operation, the first or low frequencies have a period greater than 20 seconds, and the second or medium frequency has periods of no more than one half the period of the first frequency. The changes at the second frequency are preferably interruption pulses having pulse widths not exceeding one-half of the period of the repetition of the interruptions. This is at least one perturbation during each direction or half cycle of the said first frequency. If there is only one perturbation during each half cycle, it should not occur at the ends of the half cycles of the first frequency. It should be closer to the middle of the half cycle. As more and more perturbations per half cycle are used, perturbations may be located closer to or at the ends of the cycles of the first frequency.

The period of medium frequency perturbation is not shorter than five periods of the high frequency used for generation of field direction. Generation of field direction by use of high frequency will be described later.

For large DNA above 2 megabases, the field strength in the direction of motion changes in the direction of the pulses is selected to prevent drag caused by bunching of the leading segment ahead of a corner from unduly reducing speed or resolution of separation. For this purpose, the field strength, direction, changes in direction and frequency of medium frequency pulses are selected to allow the polarized counterion sheath around the DNA to relax to a more isotropic configuration during the pulses. This prevents the counterion sheath from becoming polarized or anisotropic enough to cause the serious bunching problem described earlier. The parameters are adjusted so that the effect of the medium frequency pulses is sufficient, considering the length of the end beyond the first corner and the time duration and amplitude of the low frequency potential, to keep bunching low enough to avoid undue band spreading.

To enable the variations in direction and magnitude for this process, a PFGE system includes means for permitting the adjustability of the electric field force, electric field angle and the pulse duration to resolve DNA molecules greater than 1,000 kb and: (1) result in straight, unbent lanes for moderately large molecules; and (2) to provide minimum bunching or frictional drop of very large molecules. The means for permitting the adjustability of the electric field force, electric field angle and the pulse duration includes means for permitting adjustment of at least one of: (1) the pulse durations in a range that maintains the pulse durations shorter than one-tenth of a second; (2) the angle or angles of two fields with respect to each other; (3) the intensity of the fields; and (4) the number of repetitions of pulses of the fields before changing the angle of the two fields with respect to each other.

The straight unbent lanes as used in this description for the path of DNA is meant to distinguish movement of the strand of DNA that results in overall movement of the chromosome or fragment itself rather than changes in conformal position of different bases with respect to each other.

The words, "an unbent lane", in this specification, mean the DNA does not move substantially at an angle to the overall direction of movement so that during ten centimeters of movement with respect to the gel, the DNA does not move at an angle greater than 5 degrees to the overall motion of the DNA for a continuous distance of more than one-half centimeter nor deviate from the overall direction of movement by more than one-half centimeter measured perpendicular to the direction of movement. The terminology "no change in gross configuration" or "without change in gross configuration" or "no significant conformational change" or "no substantial flexural bending" means in this specification that the respective portions of the DNA retain their respective geometric orientation with respect to a previous observation with no more than 1 micrometer of such portions deviating by more than 40 degrees, nor 2 micrometers of such portions deviating by more than 70 degrees.

In these definitions, the time is between the previous observation and the observation in question. An instrumental criterion for forces or pulses that do not cause significant conformal change nor bent lanes is that the DNA should not migrate more than three pore diameters of the supporting medium during a single pulse. This is 0.3 micrometer for some agarose gels.

By "stiff rod" or "stiff" is meant no tendency for the DNA molecules to undergo significant conformational change during a pulse period or a series of pulse periods during which it migrates along an unbent lane in spite of collisions with particles in the gel. Many of the terms in this specification are consistent with the terminology provided in volumes 1, 2 and 3 of *Biophysical Chemistry*, by Cantor and Schimmel, W.H. Freeman and Company, N.Y., N.Y., U.S.A., the disclosure of which is incorporated herein by reference.

Drag or friction from bunching means in this specification, the increase in resistance to force tending to move the molecule forward created by bunching or retraction of the molecule from its elongated state, particularly in the leading segment beyond the first bend caused by a matrix obstruction in the path of the molecule.

In using the apparatus, the electric field parameters are adjusted in a manner specific for the DNA size range to be resolved and are preset to prevent angular lanes of migration of the DNA and to maximize resolution and speed of separation. Because the number of bends at any one time and thus the frictional drag caused by the bends is a function of a length of the molecule and density of the medium, the variable most easily controlled is the bunching effect of the leading segment of the molecule. This effect is the result of the applied potential causing displacement of the counterion sheath around the molecule from the leading end toward the first corner and the counterreaction of the molecule to it. The bunching is time and field strength dependent. Thus, variation in these factors in relation to the probable distance between the leading edge and the first corner can be controlled to maximize separation results. Generally bunching is reduced by intermittently lowering or changing the direction the electric field strength so that the counterion sheath relaxes from its previous displacement toward the first corner and becomes more uniformly distributed along the leading length of the DNA molecule. This reduces the counterreaction of the molecule because of the reduced perturbation of the local field. This, in turn, reduces the tendency toward bunching.

As can be understood from the above description, the electrophoresis apparatus of this invention has several advantages, such as for example: (1) it is able to easily separate DNA of larger size than heretofore practical; (2) it is able to separate large DNA faster than heretofore possible; and (3) it is relatively uncomplex and inexpensive.

SUMMARY OF THE DRAWINGS

The above noted and other features of the invention will be better understood from the following detailed description when read in connection with the drawings, in which.

DETAILED DESCRIPTION

Figure 1:
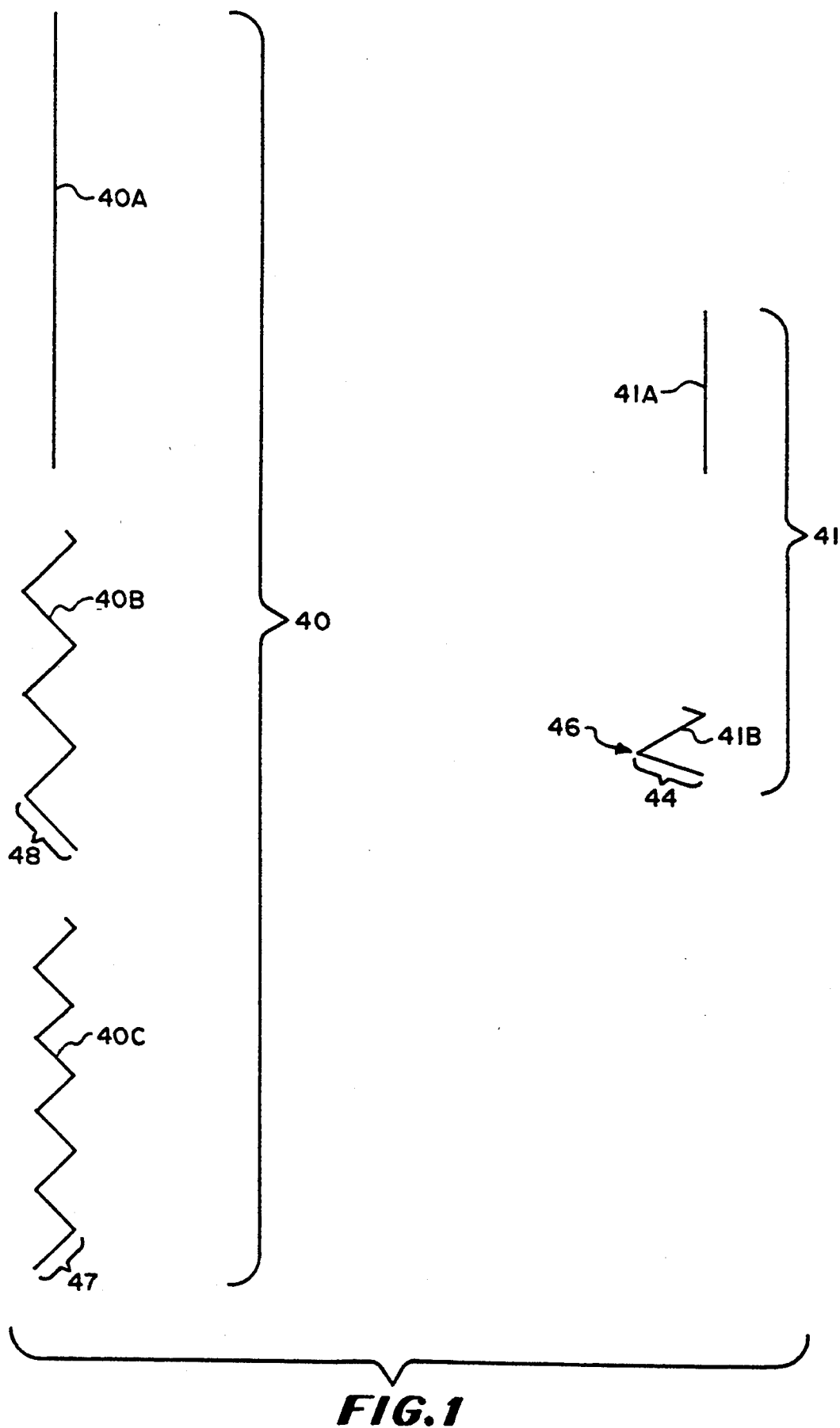
FIG. 1 is a scaled diagram of two large DNA molecules illustrating the difficulty of separation according to prior pulsed field electrophoresis techniques.

In FIG. 1, there is shown a diagrammatic view illustrating the separation of very large DNA with pulsed electrophoresis. In section 41 of FIG. 1, a straight length of a 1.5 megabase pair S. cerevisiae DNA molecule is indicated at 41A. This same molecule subjected to ordinary 120 degree pulsed electrophoresis is indicated at 41B. Calculation based on band migration speed and molecular length suggests that there should be an average of about 2.5 corners being turned by the molecule, with an appropriate selection of gel or other separating medium. These corners are a function of the length of the molecule and the obstructions in its path interacting with low frequency changes in field direction. Each corner is principally a turn toward a new field direction, with constraint from displacement away from its previous path because it is threaded through the pores in the gel.

Under these conditions, 6 volts per centimeter field and 120 seconds between 120 degree field switchings, the DNA molecule is being separated at the maximum possible speed under ordinary pulsed electrophoresis while retaining sharpness of separation. The leading length segment 44, ahead of the leading corner turning 46 is just barely short enough not to develop a seriously degrading amount of the bunching instability. If either the electric field is increased or the time duration between field switchings is increased (therefore also increasing the leading segment length), the speed of separation becomes greater but bunching instability becomes serious and the separation is degraded.

In section 40 of FIG. 1, 40A shows the extended length of the 5.7 megabase pair of DNA from S. pombe. 40B shows a contour of the 5.7 megabase DNA molecule under optimum separating conditions which are believed to be a 120 degree switching time of 30 minutes and a field strength of 1.5 volts per centimeter.

Calculation based on experimental measurement of band migration speed and on known molecular length suggests that there should be an average of about 6.3 corners turned per 5.7 megabase molecule. These bends or corners reflect the gel poreconstrained path of the molecule as it changes direction of migration in response to low-frequency direction changes of the electric field. The optimum electrical field for 5.7 megabase separation is experimentally determined to be one-fourth the optimum field for 1.5 megabase separation. The polarizability of the counterion sheath is proportional to the cube of its length along the field direction. The field for 40B for optimum migration is 1.5 volts per cm or ¼ of the field for 41B. Therefore, the optimum length of 48 (for preventing serious bunching instability of the DNA) is related to the length of 44 under optimum corner turning by a function of the cube root of 4 or 1.587 times the length of 44 which is taken as 1. Interestingly enough, this is in rough agreement with the calculation of corner turning referred to above as shown in equation 1. This is fairly close to the 6.3 corners turned for a 5.7 megabase molecule, calculated from experimental data.

The data indicates that the speed of the larger molecule is about 1/11 the speed (11 times the slowness) of the smaller molecule, whereas the field for the smaller molecule is 4 times the field for the larger molecule. This difference is believed to be due to the larger molecule turning an average of 6.3 corners and the smal let molecule turning an average of 2.5 corners, as shown in FIG. 1. Assuming an exponential relationship between the number of corners turned and the frictional force, and a linear relationship between field (and DNA strand tension) and ratio of frictional forces, we have: Force Ratio equals e to the 6.0 f power $$\frac{5.7 \text{ megabase}}{1.5 \text{ megabase}} + \frac{1}{1.587} \times 2.5 \text{ corner turnings} = \quad \text{Equation 1}$$

$$6.0 \text{ corners per 5.7 megabase molecule corners}$$

$$\text{Force Ratio} = \frac{e^{6.0f}}{e^{2.5f}} = \frac{11}{4} \text{ ; } f = 0.289 \quad \text{Equation 2}$$

$$\pm 90 \text{ degrees} + \left[ \text{ARCTANGENT} \frac{A}{B} \right] = \quad \text{Equation 3}$$

$$\text{ARCTANGENT} \frac{B}{-A}$$

divided by e to the 2.5 f power which equals 11/4. Thus, f equals 0.289 as shown in equation 2. The exponential friction factor f of 0.289 applies to each corner turned.

In FIG. 1, there is shown a contour or configuration 40C of 5.7 megabase DNA if separated at a field of 6 volts per centimeter, instead of 1.5 volts per cm (centimeter) as at 40B. To prevent excessive instability of the leading segment of DNA, its maximum length 47 can be no longer than the length 44 at 41B. This is because the field is the same for each. This results in about 9.5 average corners turned for the DNA at 40C.

Using the exponential with the constant f equals 0.289 derived above, results with the same electric field, in an increase of friction force about 2.75, calculated the ratio of the natural log base, e, for the two exponential functions e to a power of the number of turns multiplied by 0.289 e.g. (9.5 multiplied by 0.289) and (6.0 multiplied by 0.289). With a 4 times increase in field, the friction force would increase 4×2.75 or 11 times because of the increased tensioning at the corners. If this type of friction is even remotely dominant, the DNA at 40C will move even slower than the DNA at 40B. Above an optimum field strength, it does become dominant and increasing the field strength further and trying to compensate by shortening the low frequency switching time of the field will not improve the speed of separation for a given molecule or increase the maximum size of molecule that can be separated in a reasonable period of time.

It can be understood that this will be the case in a general sense as frictional force increases exponentially with the number of corners turned but the maximum permissible field or driving force only increases as the cube of the number of corners turned. However, it is well-known that, for a sufficiently large value of argument, an exponential always increases faster than any power function, so the effect of friction drag (or bunching instability) will always eventually overcome the beneficial effect of continuing to increase the field.

A conclusion derived from this explanation is that ordinary pulsed gel electrophoresis reaches an upper limit of DNA length or size which may be separated in a practical amount of time. If the preceding explanation is correct, the process could be improved by decreasing the amount of bunching or tumbling instability in the leading, free segment of DNA that is traveling ahead of the front-most corner. The leading segment is crucial because bunching is not expected to be as much of a problem behind the front corner, as each segment behind a corner is moving along a more or less fixed path through the pores of the gel medium.

It is believed that bunching instability on the leading segment of the DNA can be decreased by either more or less periodically making a short cutoff of the electric field or by making a short-duration perpendicular diversion in the field direction, quickly followed by reversion to the original field condition. These field magnitude or direction interruptions should occur multiple times during each low frequency field direction (and DNA migration direction) change corresponding to ordinary pulsed gel electrophoresis. The duration of each of these medium-frequency interruptions may advantageously be significantly shorter than the repetition time of the interruptions. The intent of the medium frequency interruptions is to decrease the electric field-produced asymmetry of the counterion sheath along linear DNA. This comes about because the anisotropy or polarization of the counterion sheath relaxes toward a more symmetrical state during the interruptions.

Figure 2:
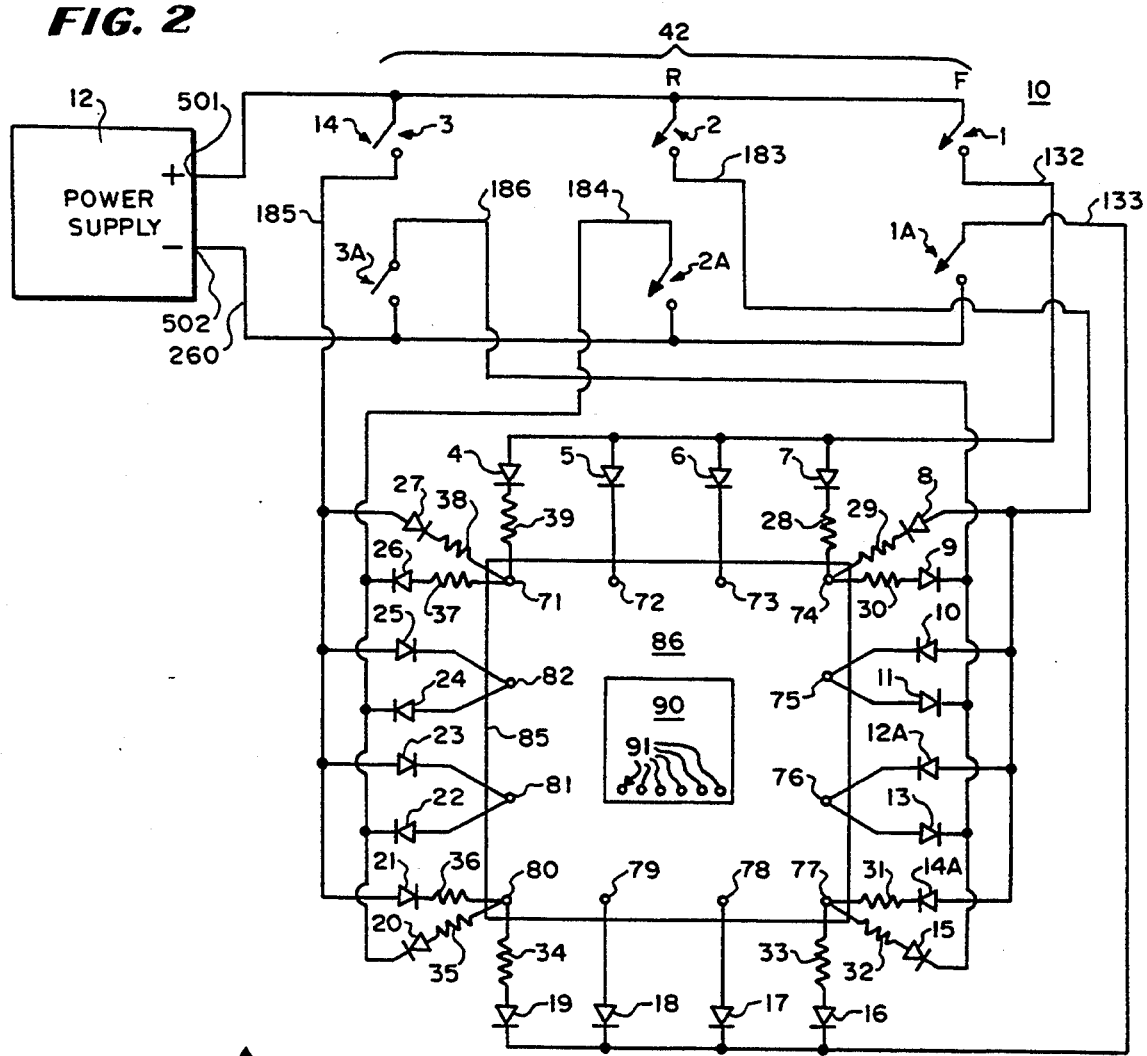
FIG. 2 is an overall schematic of a gel electrophoresis apparatus according to an embodiment of the invention.

In FIG. 2, there is shown a simplified schematic drawing of electrophoresis system 10 having a power supply 12, an electrophoresis gel system including the tank 85 and an adjustable switching means 42 connected together for controlling the electric field force, electric field angle and the pulse duration to resolve DNA molecules greater than 1,000 kb in length along straight, unbent lanes within a gel. The electrophoresis system 10 permits adjustment of the high frequency pulse periods through a range from generally 1/10 of a second to shorter ranges and generates average electric field vectors at a controllable angle by adjustment of the relative pulse widths of the two phases of high frequency pulses applied orthogonally to tank 85.

The electrophoresis gel system 10 includes the shallow electrophoresis tank 85 which is made out of insulating material adapted to contain electrolyte buffer 86. Completely submerged in this buffer is a square sheet of agarose gel 90 containing a number of wells or oval depressions 91. In these wells are plugs of gel containing mixed DNA to be separated.

To create the field in the gel separating system, electrodes 71 through 82 provide electrical contact to the buffer from the power supply 12 through the switching means 42. The electrodes are preferably made of an inert metal such as platinum.

To provide switching of the fields, the switching means 42 includes high-speed switching diodes 4 through 27, resistors 28–39 and adjustable means 15 that connect the electrodes through switching means 42 to the direct current power supply 12. The adjustable means 15 includes three sets of switches 1,1A, 2,2A and 3,3A.

To prevent interference between current paths, the diodes 4–27 are connected in three sets: (1) diodes 4 to 7 having their anodes connected to switch 1 and thence to the positive terminal 501 of the power supply 12; and diodes 16 through 19 having their cathodes connected to switch 1A and thence to the negative terminal 502 of the power supply 12; (2) diodes 8, 10, 12A, and 14A having their anodes connected to switch 2 and thence to the positive terminal 501; and diodes 20, 22, 24 and 26 having their cathodes connected to switch 2A and thence to the negative terminal 502; (3) diodes 21, 23, 25 and 27 having their anodes connected to switch 3 and from there to the positive terminal 501; and (4) diodes 9, 11, 13 and 15 having their anodes connected to switch 3A and from there to the negative terminal 502.

The electrode 71 is electrically connected to the cathodes of the diodes 4 and 27 through corresponding ones of the resistors 38 and 39 and to the anode of diode 26 through the resistor 37; the electrode 74 is electrically connected to the cathodes of the diodes 7 and 8 through corresponding ones of the resistors 28 and 29 and to the anode of diode 9 through the resistor 30; the electrode 77 is electrically connected to the cathodes of the diodes 14A and 15 through corresponding ones of the resistors 31 and 32 and to the anode of diode 16 through the resistor 33; the electrode 80 is electrically connected to the anodes of the diodes 19 and 20 through corresponding ones of the resistors 34 and 35 and to the cathode of diode 21 through the resistor 36. The cathodes of diodes 5, 6, 10, 12A, 23 and 25 are electrically connected to respective ones of the electrodes 72, 73, 75, 76, 81, and 82 and the anodes of diodes 11, 13, 17, 18, 22 and 24 are electrically connected to respective ones of the electrodes 75, 76, 78, 79, 81 and 82.

The diodes 4–27 prevent the circuits energized by switches 3,3A, switches 2,2A and switches 1,1A from interfering with each other since only one of these three switch pairs is closed at any given time and since a closed pair is always opened before the next open pair is closed. Resistors 28 through 39 limit the amount of reverse recovery current through the diodes when the switches are transferred.

Before operating the embodiment of FIG. 2, mixture of large DNA molecules are inserted into the wells 91 of the gel 90. The angle and rate of change of the angle of the fields and the pulse durations are selected in accordance with the segments of DNA that are to be separated. Other variables may play a role in this selection such as field intensity, the number of pulses between direction changes and the overall duty factor, or relative percentage of time that either of the two pulses is on, compared to the duration of the entire two-pulse cycle.

In the operation of the embodiment of FIG. 2, when switches 1,1A are closed, electrodes 71 through 74 are connected to the positive terminal of the power supply and electrodes 77 through 80 are connected to the negative terminal of the power supply. This establishes an electric field within the buffer 86 located within the tank 85.

Since the buffer covers the agarose gel 90, the electric field is also established in the gel. Under the influence of the field, negatively charged DNA starts to migrate out of the wells toward the positive electrodes, 71, 72, 73, 74.

After a very short period of time switches 1,1A open, followed by the closure of switches 2,2A. This establishes a positive potential on electrodes 74, 75, 76, and 77 through the diodes connected to switch 2A. This causes the DNA to migrate to the right. This cycle repeats very rapidly. This cycle repetition frequency is greater than 10 hertz, so the large DNA molecule does not have time to change its gross configuration during any one pulse cycle and preferably moves with a true average direction of migration as it moves with an average migration vector at an angle between horizontal movement to the right and vertical movement toward the top of FIG. 2.

After a more extended period of time, usually after more than 100 of such foregoing switch cycles have taken place, switching action stops between switches 1,1A and switches 2,2A. It immediately resumes with similar switching between switches 3,3A and switches 1,1A. When switches 3 and 3A close, positive potential from the power supply is applied to electrodes 80 through 82 and electrode 71 through diodes 21, 23, 25, and 27. Negative power supply potential is supplied through switch 3A to diodes 9, 11, 13 and 15 to electrodes 74 through 77.

When switches 3 and 3A are closed, electrodes 74 through 77 carry a negative potential and electrodes 80, 81, 82 and 71 carry a positive potential. This causes negatively charged DNA to migrate slightly or tend to migrate to the left.

A short time after switches 3,3A are closed, these two switches reopen and switches 1 and 1A close establishing a field which causes DNA to move vertically toward the top of the figure. Switches 3,3A and 1,1A alternate closing and opening very rapidly, with each switch pair opening before the other switch pair closes so that the field is uniform and applied across only one direction at a time. As earlier, this is done at a frequency greater than 10 hertz so that gross changes in DNA configuration do not occur during the switching cycle between switches 1,1A and 3,3A. However, the period of repeated alternation between switches 1,1A and 2,2A on one hand and repeated alternation between switches 3,3A and switches 1,1A on the other hand is much slower.

Preferably, more than 100 cycles of alternation between switches 1,1A and 2,2A occur before operation transfers to the alternation between switches 3,3A and 1,1A. Conversely also at least 100 alternations between switches 3,3A and 1,1A occur before operation transfers back to alternation between switches 1,1A and 2,2A. This overall cycle repeats many times during the DNA separation process. Furthermore the time pulse durations of the 1,2 alternation should be substantially equal to the time durations of the 3,1 alternation to obtain straight and well-aligned separation lanes.

Successful DNA separations with the subject invention have been made with alternation frequencies from 10 hertz to 800 kilohertz and horizontal field reversal times of from 20 seconds field trending to the right followed by 20 seconds field trending to the left followed by 20 seconds field trending to the right, and so on, on up to substantially longer times. Generally, in an embodiment in which a first pulsed electric field is applied parallel to the direction of overall DNA migration and a second pulsed electric field is applied at an angle perpendicular to the direction of overall migration, the rate of the said repetition, the direction and magnitude of the first and second pulse durations are selected in accordance with the size of the molecules being resolved wherein moderately large molecules are separated with an average field which periodically changes direction at a low frequency and large molecules are separated with a field which periodically changes direction at a low frequency but incorporates additional higher frequency perturbations that reduces bunching.

More significantly, successful very large DNA separations with the subject invention have been made with alternation frequencies from 50 kilohertz to 800 kilohertz and crossways field reversal times of from 60 seconds field trending to the right followed by 60 seconds field trending to the left followed by 60 seconds field trending to the right, and so on, on up to longer times such as 3,000 seconds in each direction. At times on the order of 200 seconds and longer and at alternating frequencies of 50 to 800 KHz, whole chromosomes from yeast species *S. Cerevisiae* (200 to 2,000 kb) and *S. pombe* (3,000 to 5,700 kb) have been separated. However, these separations are difficult and require 3–5 days without the medium-frequency field interruption pulsing discussed earlier, and to be described in detail later.

The electrophoresis tank 85 shown in FIG. 2 is drawn in a simplified form to illustrate the principle without confusing complexity in the diagram. In a preferred embodiment: (1) the tank is 20 cm square inside; (2) the agarose gel 90 is 10 cm square by about 4 mm thick, is located in the center of the tank and is completely immersed in the buffer 86 to a depth such that its top surface is at least 1 mm under the sur face of the buffer. The forward and crossways fields in the tank 85 are determined by measuring the potential between electrodes 72–79 and 76–81, respectively, and dividing by 20 centimeters. Preferably, this is done using DC voltmeter leads that are isolated with 1 megohm resistors at their measuring tips.

Instead of four electrodes on each side of the tank, eight electrodes are used to make the electric field within the buffer more uniform. All electrodes are wired as shown in the figure. There are of course still only four sets of three diodes, one set connected to each of the four corner electrodes in the tank. However, there are six intermediate electrodes on each of the four sides of the tank between the corner electrodes. They are wired exactly as shown for each of the four sets of the two side electrodes in the figure.

Since alternation frequencies up to at least 800 kilohertz are useful with this apparatus, the diodes 4 through 27 are high frequency, fast-switching diodes such as type 1N4448 diodes. The 1N4448 has a reverse recovery time of just 4 nanoseconds, combined with good overload capability.

Since the reverse voltage rating of the 1N4448 diode currently being used is only 75 volts, four diodes are used in series in each of the diode positions shown in FIG. 2. The resultant voltage rating of 300 volts is more than adequate for use on the relatively small 20 cm square tank used for electrophoresing 10 cm square gels.

Figure 3:
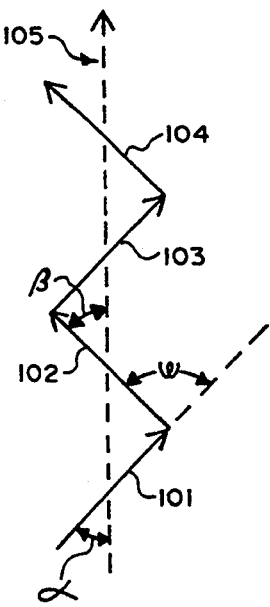
FIG. 3 is a schematic fragmentary view within a electrophoresis gel illustrating the vector direction of the fields and the path that would be taken by DNA in many PFGE systems.

In FIG. 3, there is shown an exposition of the path of the DNA molecule as it migrates in the gel 90 (FIG. 2) having a general direction of migration indicated at 105, and several vectors of motion shown at 101–104 for illustration purposes.

To obtain the overall direction of migration 105, several angled migration vectors are alternately created in directions which results in the overall migration direction. As shown in FIG. 3, one of these migration vectors, vector 101, is formed from a series of pulses caused by the rapid opening and closing of switches 1,1A and 2,2A alternately as described in connection with FIG. 2. The frequency of alternation between high-frequency switchings is high enough so that the migration behaves substantially as if the field were continuous.

At the arrowhead end of migration vector 101, switches 1,1A (FIG. 2) stop alternating with switches 2,2A (FIG. 2), and switches 3,3A (FIG. 2) begin alternating rapidly with switches 1,1A. This changes the DNA's migration to the migration vector labeled 102. Again the alternation frequency is high enough so that the DNA molecule migrates substantially as if it were in a continuous field when moving along vector 102.

After a selected period of time of migration along vector 102, equal to the time of migration along vector 101, the alternation sequence changes back to that that took place from migration vector 101 formed by the rapid alternation between closures of switches 1,1A and 2,2A. During this time, the large DNA molecule moves along vector 103 in a manner similar to that as if it were in a continuous field rather than a perpendicularly pulsing field. A further reversal takes place at the arrowhead end of vector 103 and migration continues along vector 104, etc. The resulting overall migration is upwards along the average path 105.

The effect from switching from vector 101 to vector 102, from vector 102 to 103 and from vector 103 to 104, and so on is to provide differentially lower mobility for large DNA compared to small DNA. It is this slow, overall obtuse angle change in migration vector which provides differential mobility necessary for the separation of large DNAs.

In the subject invention, a large number (preferably over 100) 90-degree high frequency field alternations take place to form each field migration vector and the 90-degree alternations forming the migration vector take place at a frequency greater than 10 hertz. Migration vector 101 is inclined by the angle alpha to the direction of overall migration 105. Migration vector 102 is inclined by the angle beta to the direction of overall migration 105. Migration vector 102 makes an angle of omega with respect to vector 101.

The relative enhancement of DNA-gel interaction due to the submicroscopically vibrating direction of migration during pulsing is believed to enhance this differential by increasing the sieving effect in a manner related to the size of the molecule in addition to the time spent realigning the molecule due to horizontal field reversal. The stability of the gross configuration during one pulse cycle is believed to further enhance this effect. It is believed that these enhancement effects account for faster resolution of large DNA.

The movement of the large DNA strand is in an unbent lane of movement 105. The words, "an unbent lane", in this specification, mean the DNA does not move substantially at an angle to the overall direction of movement so that during ten centimeters of movement with respect to the gel, the DNA does not move at an angle greater than 5 degrees to the overall motion of the DNA for a continuous distance of more than one-half centimeter nor deviate from the overall direction of movement by more than one-half centimeter measured perpendicular to the direction of movement. The terminology "no change in gross configuration" or "without change in gross configuration" or "no significant conformational change" or "no substantial flexural bending" means in this specification that the respective portions of the DNA retain their respective geometric orientation with respect to a previous observation with no more than 1 micrometer of such portions deviating by more than 40 degrees, nor 2 micrometers of such portions deviating by more than 70 degrees.

In these definitions, the time is between the previous observation and the observation in question. An instrumental criterion for forces or pulses that do not cause significant con formal change nor bent lanes is that the DNA should not migrate more than two pore diameters of the supporting medium during a single pulse. This is 0.2 micrometer for some agarose gels. By "stiff rod" or "stiff" is meant no tendency for the DNA molecules to undergo significant conformational change during a pulse period or a series of pulse periods during which it migrates along an unbent lane inspite of collisions with particles in the gel. Many of the terms in this specification are consistent with the terminology provided in volumes 1, 2 and 3 of *Biophysical Chemistry*, by Cantor and Schimmel, W.H. Freeman and Company, N.Y., N.Y., U.S.A., the disclosure of which is incorporated herein by reference.

In the subject invention, a large number (preferably over 100) 90-degree field alternations take place to form each field migration vector and the 90-degree alternations forming the migration vector take place at a frequency greater than 10 hertz. Migration vector 101 is inclined by the angle alpha to the direction of overall migration 105. Migration vector 102 is inclined by the angle beta to the direction of overall migration 105. Migration vector 102 makes an angle of omega with respect to vector 101.

Angle omega is equal to the sum of angle alpha plus angle beta. The angle alpha of vector 101 is equal to the angle beta of vector 102 since the relative time durations of the switching of switches 1,1A and 2,2A are the same as that for switches 3,3A and 1,1A. Since angle alpha equals angle beta, the angle omega is equal to two times angle (alpha or beta). It is usually preferable to operate with an angle omega equal to about 120 degrees.

While perpendicular fields are used in the preferred embodiment, other fields acting at angles to each other may be used provided the pulses do not change the overall DNA configuration, the time between pulses does not relax (allow time to change the configuration of) the DNA, the changes in direction of the pulses or polarity of the fields does not unduly bend the lane, and the resultant motion is along a predictable lane permitting comparisons between lanes. Moreover, the pulses in the orthogonal fields or fields that are at angle to each other need not alternate on a one-to-one basis but other ratios may be used such as two pulses perpendicular to the direction of migration to each pulse at an angle along the direction of migration.

The frequencies of pulses to be used and the periods of time between reversals of polarity of the angled fields may be selected more carefully for individual cases by trial in error since the values and ranges given herein were selected because of results on only some tests with certain DNA strands.

Figure 4:
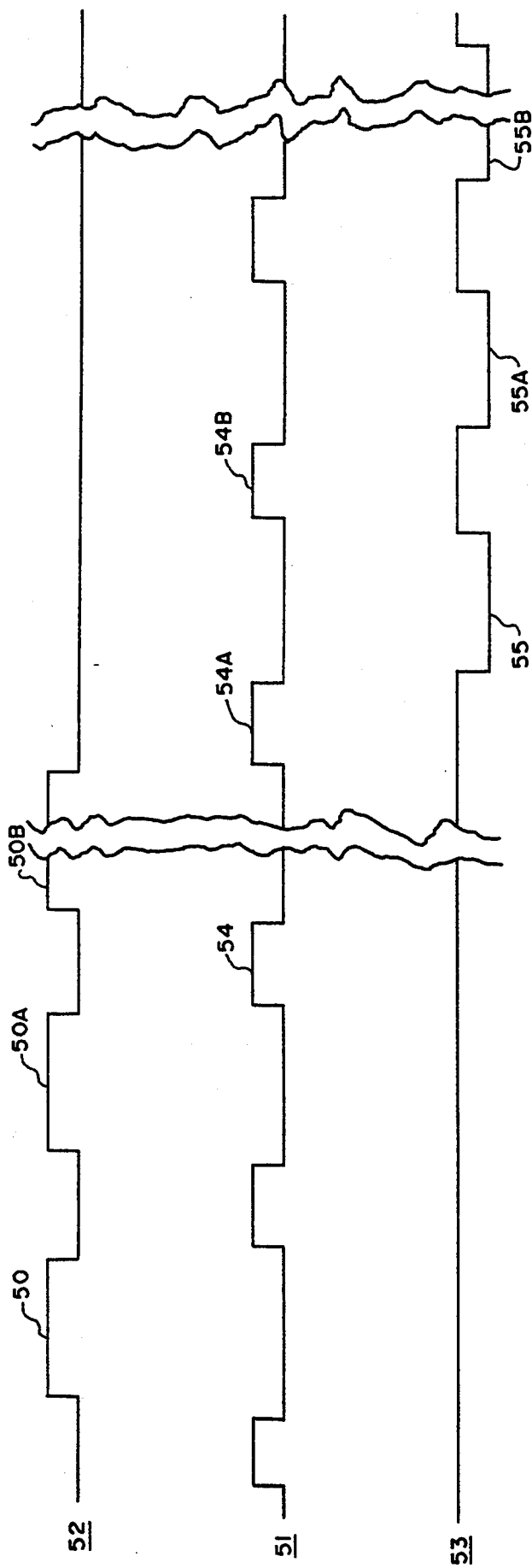
FIG. 4 illustrates the pulsed timing of voltages applied to an electrophoresis tank in accordance with the embodiment of FIG. 1.
Figure 6:
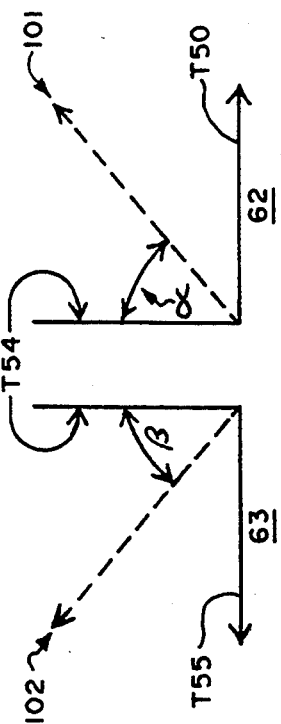
FIG. 6 represents variable angle migration vectors generated by two perpendicular, time shared fields in accordance with an embodiment of the invention.
Figure 5:
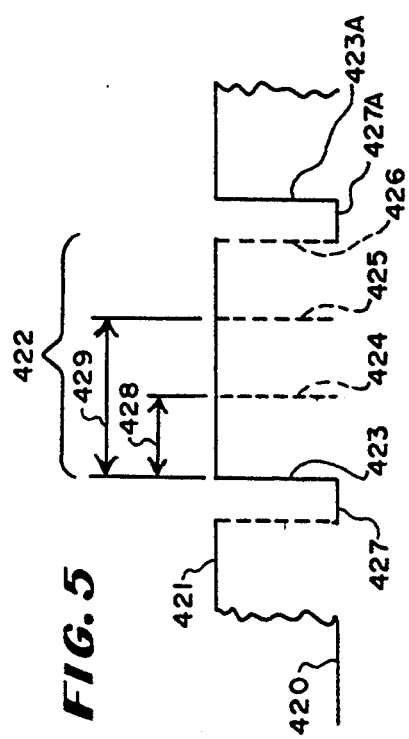
FIG. 5 illustrates relative pulse duration or duty factor of a pulse generator used to generate the pulses of FIG. 2.

In FIG. 4, FIG. 5 and FIG. 6, there are shown diagrams illustrating the manner in which the angle of migration is varied using the method of the invention. In FIG. 4, there is shown a graph of field intensity against time having ordinates of intensity and abscissae of time illustrating the relationship of the timing of the switch closures in the switching device 42, which are curves of: (1) switching a pattern 51 corresponding to the time of the closing and opening of switch pair 1,1A; (2) switching pattern 52 corresponding to the time of the opening and closing of switch pair 2,2A; and (3) switching pattern 52 corresponding to the timing of the opening and closing of switch 3,3A. Each of the paired switching patterns 51–52 and 53–52 may be considered a 2-phase pair, and each 2-phase pair is used to generate an average field vector in the tank 85.

In curves 51 and 52 in FIG. 4, the pulses 54, 54A, and 54B represent closure time of switch pair 1,1A; and 50, 50A, 50B represent closure times of switch pair 2,2A. The switch closures alternate in time as shown at 51 and 52, with a short duration of time (for example, in the hundred nanosecond region) between stitch closures, during which time all switches are open so that no set of switches from a given side are closed at the time of switches from another side and the field is always in one direction. The field is alternately along the general overal direction of migration 105 and from an angle to the direction of migration. This switching pattern produces a migration vector at a rightwards angle (101 in FIG. 2). Switch 3,3A stays open during this migration at a rightwards angle.

Switch 2,2A opens and stays open during horizontal field reversal for migration at a leftwards angle. This migration entails the alternation of closures between switch pairs 3,3A and 1,1A is shown in FIG. 4 at 51 and 53. Switch pair 3,3A is connected to provide opposite field polarity in electrophoresis tank 85 compared to switch pair 2,2A. Therefore the polarity of the pulses shown at 53 are inverted, producing a DNA migration vector at a leftwards angle (102 in FIG. 3A) instead of a rightwards angle.

The closure durations of switch pair 3,3A are shown as 55, 55A, 55B and switch pair 1,1A is open at these times. Closure durations of switch pair 1, 1A are shown as 54, 54A, 54B, and switch pair 3,3A is open at these times. As was the case for switch pairs 1,1A and 2,2A, there is a short period of time, on the order of hundreds of nanoseconds, after the time one pair of switches 1,1A and 3,3A opens, before the other pair of switches closes. This time is kept sufficiently short to ensure that there are no configurational changes of the DNA between pulses and to keep from significantly decreasing the average voltage. The time between pulses depends on the size of the DNA strand but generally should be less than one second and more commonly are in the microsecond or nanosecond ranges.

The angle omega, which is the angle between one migration vector to the next, is changed by varying: (1) the ratio between pulse lengths 50 and 54; and (2) the ratio between pulse lengths 55 and 54. These two ratios are generally equal and pulse length 50 is kept equal to pulse length 55. This is controlled by a variable-duty factor pulse generator whose output is shown in FIG. 5.

In FIG. 5, there is shown the output of this pulse generator, having two states: a low state 420 and a high state 421. The pulse generator operates continuously and repetitively with the pulse cycle shown as 422. The pulse starts from low and rises or goes high as indicated at 423.

The pulse generator is set or programmed to any constant frequency between 10 hertz and 1 megahertz. By means of an adjustable duty factor setting, it produces a more or less infinitely variable pulse time width percentage which width can be set from substantially zero to the period of one cycle of the pulse generator frequency. Pulse falls indicated as 424, 425 and 426 indicate three of the many possible pulse durations. The pulse fall at 424 produces the pulse duration 428, a pulse fall at 425 produces the pulse generation 429, and so forth. Due to limitations in the pulse generator it may not be possible to attain an output that is continuously high as indicated at 421.

Between pulse cycles there may be a short period of low voltage such as 427 and 427A. Commercially pulse generator circuits are available in which this "dead time" is so small as to be negligible for the purposes of the invention. The pulse output of FIG. 2 is used to generate the pulse pattern of FIG. 4.

When the output is high as shown at 421 one of switch pairs 2,2A or 3,3A is closed and switch 1,1A is opened so that the instantaneous electric field is crossways (perpendicular in the preferred embodiment) to the overall direction of migration. When the output the pulse generator is low as shown at 420, both switch pairs 2,2A and 3,3A are turned off and switch pair 1,1A is turned on, producing a field such as 54 parallel to the overall direction of migration. The setting of the angle is determined by the duty factor of the pulse timing: the ratio time for which pulses 50, 50A, 50B or pulses 55, 55A, 55B are "on" compared to the time that pulses 54, 54A, 54B are "on". This is illustrated in FIG. 6.

In FIG. 6, there are shown two two-dimensional vector diagrams relating to the pulse duration relationships 62 existing between 51 and 52 (FIG. 2) and the relationship 63 between 51 and 53. In diagram 62, the length of vector T50 corresponds to the relative time duration of pulses 50, 50A, 50B and the length of vector T54 corresponds to the relative time duration of the pulses 54, 54A, 54B. In diagram 63, vector T55 corresponds to the time duration of pulses 55, 55A, 55B and vector T54 is the same as in diagram 62.

If there are no significant changes in DNA configuration between a pulse period composed of pulses 50 and 54, there will be no change in electrophoretic mobility over the pulse cycle. The conformational changes due to conventional low frequency pulse duration patterns affect short term electrophoretic mobility. However it has been discovered that if the pulses are fast enough, unprecidentally fast for gel electrophoresis of large DNA, there is either no gross change in DNA configuration for some size DNA during the pulse cycle and no significant change in mobility during the pulse cycle in some sizes of DNA or the changes may with proper preparation improve resolution of the DNA.

With the mobility constant over the pulse period, migration may be treated as a linear, time-invariant system. The resultant migration vector for rapid pulse alterations repeated numerous enough times may be treated as the two-dimension vector sum of the relative pulse durations. This is indicated as the migration vector 101 shown in vector diagram 62 of FIG. 6. The vector component T50 corresponds to the relative time in which the field is perpendicular to the direction of migration, with migration to the right in the gel 90. The angle alpha in diagram 62 corresponds to the angle alpha in FIG. 3. The vector component T55 (diagram 63) is equal and opposite to vector component T50, so the perpendicular directions cancel with respect to the path of the lane in the overall DNA separation. The direction T54 is the overal 1 direction of migration (105 in FIG. 3).

Diagram 63 shows time durations T54 and T55 used as component vectors to generate the migration vector 102. As with diagram 62, this is only correct if the switching frequency between the pulses 54 (FIG. 3) and 50 or 55 are fast enough so that there are significant configurational changes in the DNA during the pulse cycle.

If the slow alteration period described by Schwartz, D.C., and Kovel, M. (1989), "Conformational Dynamics of Individual DNA Molecules during Gel Electrophoresis," *Nature* 338:520–522 were used, it would be difficult to define vectors 101 and 102 since electrophoretic mobility would not be constant during the pulse alternation cycle due to conformational changes of the DNA. Under the influence of a suddenly applied electric field, the DNA develops conformational change over a period of time. The instantaneous mobility depends upon conformation change which increases with both field and time.

If the DNA is in a field which is perpendicularly pulsed repeatedly and relatively slowly (on the order of seconds) the conformation differs significantly between the beginning and end of each pulse. This is not a self-cancelling effect since the perpendicular pulse pattern is repeated over a number of identical cycles. Mobility will be time and voltage dependent and a true migration vector cannot be developed.

Operation at sufficiently high frequencies (greater than ca. 10 kilohertz) tends to suppress secondary effects of the instantaneous field on the DNA such as flexural bending due to electrostatic induction of dipoles in the DNA. In aqueous buffer, above 10 kilohertz, the relaxation time ("time constant") of movement of even a segment of DNA is so short that it behaves somewhat like a stiff rod and tends to be slower than the period of field alternation.

At such high frequencies, the viscous friction of the buffer within the surrounding pores of the agarose gel opposes bending of the DNA, even on a minute scale, as the perpendicular field alternates. Since the length of a DNA segment that begins to act stiff is about 60 nanometers, and the pore size in agarose gels is about 150 nanometers, varying the pulse frequency above or below 10 kilohertz can advantageously affect the separation by varying the DNA/gel interaction.

At higher frequencies, only a very short and quite stiff segment of DNA can move against the buffer viscosity. At such high frequencies, the viscous friction of the buffer within the surrounding pores of the agarose gel opposes bending of the DNA, even on a minute scale, as the perpendicular field alternates.

As shown in FIG. 6, the angles alpha and beta are each equal to the arctangent of the time period of the crossways field multiplied by the voltage at that time, divided by the time period of the forward field (field along the direction of average overall migration) multiplied by the vol rage at that time. The time period is multiplied by the pulse voltage because the DNA movement is the product of the two, since with high frequencies there are no significant conformational changes in the DNA during each pulse. Accordingly, the DNA mobility is constant over the pulse cycle. If the pulse voltage is constant, as in a preferred embodiment, its effect cancels out with respect to the angles alpha and beta.

Since the angle omega (FIG. 3) equals alpha plus beta, omega equals two times the arctangent of the time of one crossways pulse divided by the time of one pulse in the direction of overall migtation. Thus, the angle omega can be set from essentially zero up to 180 degrees by varying the duty factor of a pulse generator to produce variable width pulses as illustrated in FIG. 5.

Figure 7:
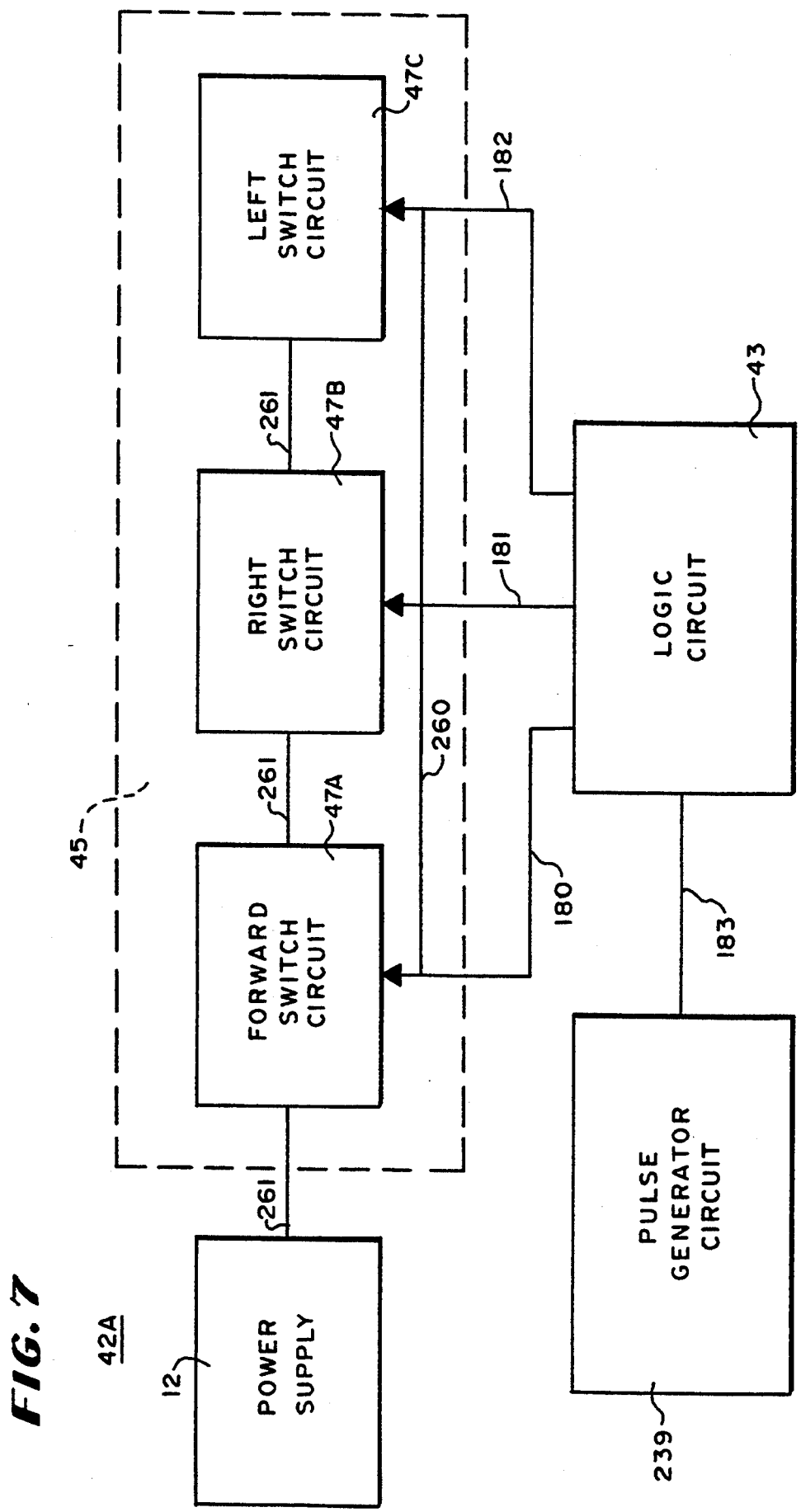
FIG. 7 is a block diagram of a switching arrangement.

In FIG. 7, there is shown a block diagram of an early version switching mechanism 42A indicated as 42 in FIG. 2 having: (1) a power supply 12; (2) a switching mechanism circuit 45 with a forward switch circuit 47A, a right switch circuit 47B and a left switch circuit 47C; (3) pulse generator circuit 239; and (4) logic circuit 43. This circuit performs well when operating at frequencies up to 70 kilohertz.

The power supply 12 is connected to the switch circuits 47A, 47B and 47C in the switching mechanism circuit 45 through conductors 260 and 261. The logic circuit 43 is connected to: (1) pulse generator circuit through cable 183; (2) left switch circuit 47C through conductor 182; (3) right switch circuit 47B through conductor 181; and (4) forward switch circuit 47A through cable 183 to conductor 180.

The switching mechanism 42A operates similarly to the switching mechanism of the preferred embodiment, and in the interest of simplicity it will be explained first.

Figure 8:
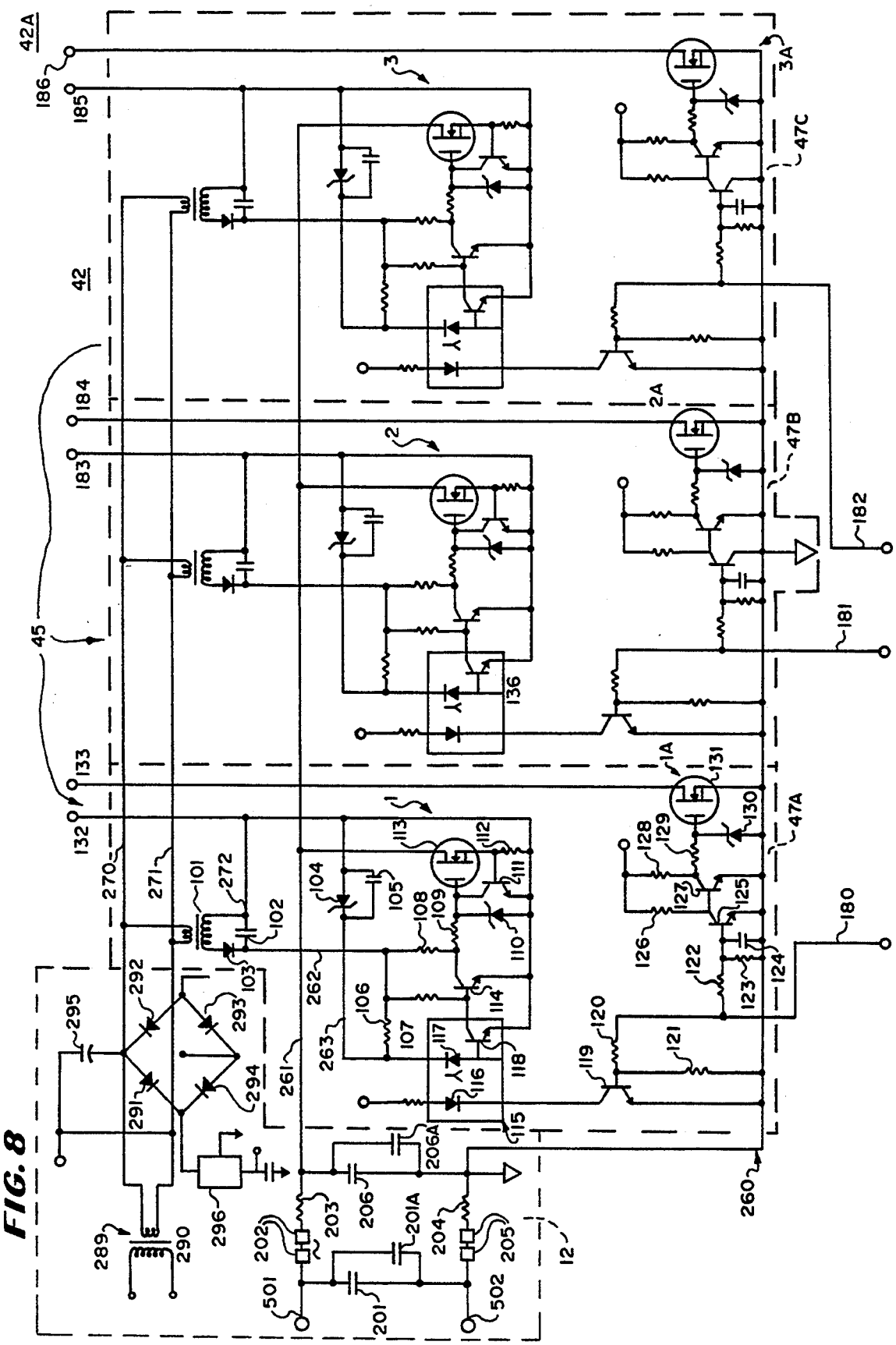
FIG. 8 is a schematic diagram of a portion of the embodiment of FIG. 7.
Figure 9:
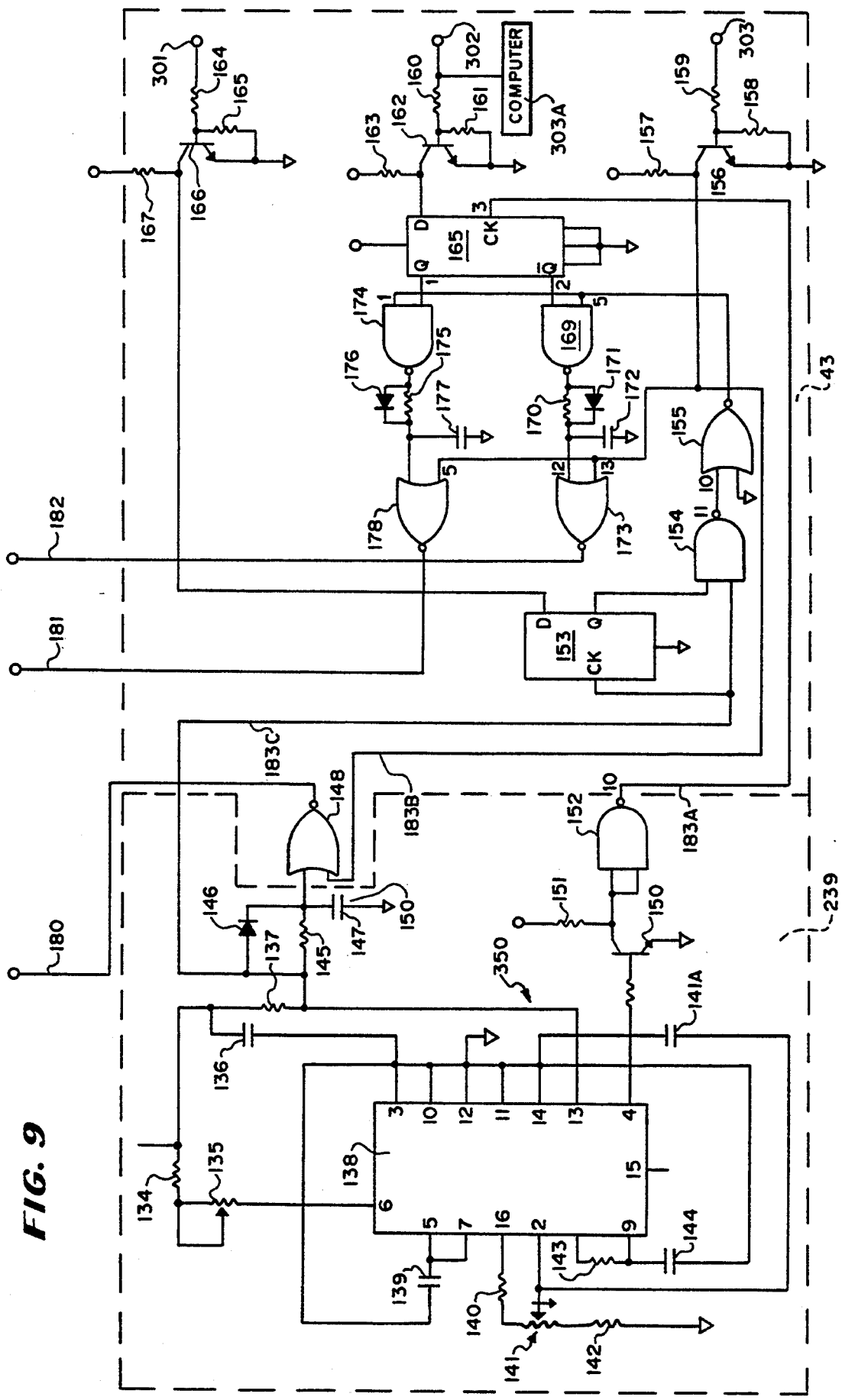
FIG. 9 is a schematic diagram of another portion of the embodiment of FIG. 7.

In FIG. 8, there is shown an electrical schematic drawing of the power supply 12 and the switching mechanism circuit 45 and in FIG. 9, there is shown an electrical schematic drawing of the pulse generator circuit 239 and logic circuit 43.

The switching mechanism 42A incorporates: (1) a pulse generator integrated circuit 138 and its ancillary pulse generator circuitry 239 (FIG. 9); (2) logic circuitry 43 (FIG. 9); and (3) switching mechanism circuitry 45 with the switches themselves indicated as 1,1A, 2,2A and 3,3A in a forward switch circuit 47A, a right switch circuit 47B and a left switch circuit 47C (FIG. 8). The logic circuitry 43 is made of CMOS, NAND gates type 4011B, NOR gates type 4001B, D flip-flops type 4013B plus ancillary discrete logic circuitry.

The variable width pulse generator 138 (FIG. 9) produces a pulse of continuously variable duty factor from 0 percent to almost 100 percent at a frequency that may be selected between 10 hertz to over 100 kilohertz and is a Silicon General integrated circuit type 3525A used in a circuit taken from applications literature provided by that company.

In this circuit, capacitor 139 (FIG. 9) determines the general frequency range selectable by variable resistance 135 in series with the fixed 4.7K resistor 134 (FIG. 9) . A wide range of pulse frequencies may be selected with a conventional switch (not shown) for selecting different values for capacitor 139 (FIG. 9) to cover the 10 hertz to over 100 kilohertz frequency range for creating the field alternation rates useful for this apparatus in a manner known in the art. For example, with a 0.0022 microfarad capacitor 139, a 100K ohm variable resistor 135 and a 4.7K ohm resistor 134, a frequency range of about 5 to 100 kilohertz results from adjusting the value of variable resistor 135. A 0.044 microfarad capacitor provides a frequency range of 250 hertz to 5 kilohertz, etc. The frequency corresponds to the period (50+54) or (55+54) in FIG. 4, the frequency of one complete perpendicular switching cycle of the fields.

To set the duty factor of the pulse generator's output pulse, a ten-turn potentiometer 141 is connected in series with 301 ohm and 500 ohm resistors 140 and 142 to vary the voltage on pin 2 of the integrated circuit 138 (FIG. 9) . The 1K resistor 143 and 0.047 capacitor 144 provide stability compensation for the error amplifier in integrated circuit 138 and the 0.1 microfarad capacitor 141A bypasses noise from the duty factor setting input at pin 2 (FIG. 9).

The output from the pulse generator integrated circuit 239 is taken from pin 13 of the integrated circuit 138 (FIG. 9) so as to provide a 0 to almost 100 percent duty factor instead of a 0 to 50 percent duty factor available from other outputs. This 0 to almost 100 percent output is on lead 350 which is supplied with pull-up resistor 137 to raise lead 350 to a high (+15 volts) logic level when current does not flow into pulse generator 138 through pin 13 (FIG. 9). When current flows through pin 13, this pulls potential on lead 350 to a low logical level near 0 volts.

To control the field in the electrophoresis tank 85 (FIG. 2), the logic circuitry 43 includes the control inputs 301, 302 and 303 (FIG. 9) which are connected so that: (1) control input 303 turns the field in the electrophoresis tank on and off; (2) a conventional switch (not shown) is connected between circuit 303 and the +15 volt supply for the user to turn the field on and off; and (3) a personal computer 303A programmed as a conventional repeating interval timer, which may be similar to like arrangements often used in the pulsed electrophoresis art (e.g., Bancroft, I., and Wolk, C.P. (1988); BIOTECHNIQUES 7 7405–7418), is connected to terminal 302 to control the longer-time durations of the migration vectors (101, 102 in FIG. 3). This timer has a fixed 50 percent duty factor.

A conventional switch (not shown) is connected between terminal 301 and +15 volts. When this switch is closed, the field perpendicular to the direction of overall migration is switched off and only the field parallel to this direction is left on. This is a diagnostic feature intended for investigation of migration properties during experimental use or evaluation of the apparatus.

When terminal 303 is at a logical high voltage, the collector of transistor 156 is low, pulling low: the pin 5 input of switch-controlling NOR gate 178, the pin 12 input of switch-controlling NOR gate 173 and the pin 2 input of switch-controlling NOR gate 148 (FIG. 9). This enables these three NOR gates to turn on the respective switch pairs 2,2A, 3,3A and 1,1A. The NOR gates are types 4001B.

Each of the switch pairs 1,1A, 2,2A and 3,3A (FIG. 8), three sets of switches, driving gates and related circuits are identical and operate in an identical manner. Thus, only switch-controlling NOR gate 148 and switch pair 1,1A, will be described in detail.

In switch pair 1,1A, the switch elements 1 and 1A (FIG. 8) themselves are n-channel MOSFET enhancement-mode power transistors, Motorola Type MTP1N60. This transistor was selected because it is capable of handling up to 600 volts and 1 ampere, more than sufficient for the application. It is not desirable to use a higher current transistor for this application, even apart from cost, because the higher gate capacitance of a larger transistor makes submicrosecond switching times difficult. The transistors are indicated as 113 and 131 in FIG. 8. The drain of transistor 113 is connected through lead 261 to the positive terminal 501 of power supply 12 (FIGS. 2 and 8).

The power supply 12 is decoupled by switching transient suppressor elements comprising 0.05 microfarad, 600 volt capacitors 201, 201A, 206 and 206A, ferrite beads 202 and 205, and 4.7 ohm resistors 203 and 204 (FIG. 8). These filter elements prevent switching transients from transistors 113 and 131 (or any of the other MOSFETs) from disturbing the regulation of power supply 12 (FIG. 8). Transistor 131 has its source connected to common potential lead 260 (FIG. 8). This makes its gate drive circuit simple as the gate drive circuit may also be referenced to common potential. However, transistor 113 has its source connected through current limiting resistor 112 to the positive parallel direction field output terminal and lead 132 (FIGS. 2 and 8). The voltage at this terminal changes very rapidly and frequently as the apparatus operates and therefore the gate drive for this MOSFET transistor must be isolated.

To this end, a Type 6N136 optoisolator 115 has been used as shown in FIG. 8 to isolate the gate drive of transistor 113 from the logic circuitry. The isolation of rapid voltage changes by the 6N136 optoisolator 115 between its input light emitting diode 116 and its output circuitry 117 and 118 is limited by internal capacitance effects. The 6N136 optoisolator 115 is useful only for power supply 12 for voltages up to about 200 volts because of the fast switching speeds used.

The preferred embodiment uses a Hewlett-Packard HCPL-2411 optoisolator which has much better "dv/dt" (high speed, high switching voltage) isolation. The HCPL-2411 is wired slightly differently from that shown in FIG. 6, as indicated in Hewlett-Packard optoisolation product literature.

When the pulse output lead 350 from the pulse generator 138 goes high, capacitor 147 charges very rapidly (much faster than one microsecond) through diode 146 (FIG. 9). The rise in potential on pin 1 of NOR gate 148 (FIG. 8) brings its output lead 180 (FIGS. 8 and 9) low. This quickly turns off transistor 119 by removing the supply of base current through resistor 120 (FIG. 8).

With collector current no longer flowing through transistor 119, light emitting diode 116 in optoisolator 115 turns off (FIG. 8). Current stops flowing through optically coupled photodiode 117, turning off transistor 118 within optoisolator 115 (FIG. 8). Current flowing through resistor 107 then flows through the base of transistor 114 turning it on (FIG. 8). This discharges the gate capacitance of power MOSFET 113 through resistor 109, very rapidly turning off MOSFET 113; and opening switch 1 (FIG. 8).

Simultaneously, the low voltage on lead 180 turns off transistor 125 which has been receiving base current from resistor 122 (FIG. 8). Capacitor 124 is connected between the base and emitter of transistor 125 to simulate the time delay associated with optoisolator 115, so that transistor 125 turns off at substantially the same instant that transistor 118 turns off (FIG. 8). The turn-off of transistor 125 allows current through resistor 126 to flow into the base of transistor 127, discharging the gate capacitance of MOSFET 131 and thus very rapidly turning switch 1A off and opening switch 1A at the same time as the opening of switch 1 (FIG. 8).

Later in the pulse cycle when the output of pulse generator 138 on lead 350 becomes low, capacitor 147 discharges through resistor 145 (FIG. 9). This takes 1 to 1½ microseconds and after this time, the output lead 180 of NOR gate 148 goes high (FIG. 9). (There is no such delay in the previous or following part of the pulse cycle when lead 180 (FIGS. 8 and 9) goes low thereby turning off switches 1 and 1A (FIG. 8)). However, there is a 1 to 1½ microsecond delay before lead 180 goes high, thereby turning switch pairs 1 and 1A on (FIG. 8).

Since all three of the switch pairs 1,1A, 2,2A and 3,3A (FIG. 8) are controlled through a similar fast turn-off, slow turn-on circuits, the result is that on each transition, the previous switch turns off 1 to 1½ microseconds before the next switch turns on thereby avoiding short circuits.

When switches 1,1A are turned on and lead 180 goes high, transistor 119 turns on by means of base current supplied through resistor 120 (FIG. 8). This lights LED 116 in optoisolator 115 turning on photodiode 117 and amplifying transistor 118 (FIG. 8). Current through the collector o#transistor 118 brings the base transistor 114 (FIG. 8) low and it turns off. The gate capacitance of MOSFET 113 charges up through 15 kilohm resistor 108 until it reaches a potential of about +10 volts, where zener diode 110 clamps it at that level (FIG. 8). MOSFET 113 (FIG. 8) turns on as the gate swings up past about +5 volts. Meanwhile, the high level on lead 180 (FIGS. 8 and 9) turns on transistor 125 with base current through resistor 122 (FIG. 8). Capacitor 124 (FIG. 8) delays this operation to match the time delay associated with optoisolator 115 (FIG. 8) so that both switches 1 and 1A (FIG. 9) turn (an off) at the same time.

For switch 1, 5.6 volt, zener diode 104 and capacitor 105 set a regulated potential for operating the photodiode 117 in the optoisolator 115 (FIG. 8). Zener diode bias is supplied by 100 kilohm resistor 106 (FIG. 8). Overcurrent damage to transistor 113 (and transistor 131 which is effectively connected in series with it) is prevented by resistor 112 and transistor 111 (FIG. 8). If the current exceeds 0.8 ampere, the voltage drops across resistor 112, turns on transistor 111 shorting to the gate of MOSFET transistor 113 to a low potential tending to turn it off (FIG. 8). This description also applies to switch pairs 2,2A and 3,3A as well as switch pair 1,1A (FIG. 8).

To electrophoretically separate DNA larger than one million base pairs in size, ordinary pulsed electrophoresis of large and very large DNA utilizes times between changes in field direction ranging from about one minute to one hour. The disclosed invention superimposes field perturbations having time durations on the order of 100 to 1000 milliseconds at repeating intervals on the order of 1 to 15 seconds. This enables a very significant increase in the speed of separation and in the maximum size of DNA that may be separated on a practical basis. Complete chromosomes of the yeast *Schizosaccharomyces pombe* (972) and of the fungus *Colletotrichum trifolii* can be separated in less than 20 hours.

All transistors in FIGS. 8 and 9 are type 2N3904, with the exception of the MOSFETs MTP1N60 and the transistors in the optoisolators. Switch turn-off before the next switch turn-on is primarily provided by the resistor-diode-capacitor networks 145-146-147, 175-176-177 and 170-171-172, respectively at the inputs of NOR gates 148, 178 and 173 (FIG. 8). They cause each of the respective switch pairs 1,1A, 2,2A and 3,3A (FIG. 8) to turn off about 1 to 1.5 microseconds before the next one starts to turn on.

The size of resistors 108 and 126 in switches 1 and 1A is sufficiently large so that the turn-on time of the MOSFET transistors 113 and 131 is about ½ microsecond (FIG. 8). This also applies to the MOSFETs in switches 2, 2A, 3 and 3A (FIG. 8). Shorter turn-on times than ½ microsecond provide some degree of problems with transient reverse recovery currents through the diodes connected to the electrophoresis tank 85 (FIG. 2). The MOSFET turn-off times, which are set by the resistors 109 and 129 in switches 1 and 1A (and corresponding resistors in switches 2, 2A, 3 and 3A), are about three times as fast as the turn-on times to provide further ensurance that one pair of MOSFET switches turns off before the next pair turns on.

The gates of switch 1 (and of course also switches 2 and 3) (FIG. 8) and associated driving circuitry operate from an isolated power supply. Each such isolated supply is derived from low voltage AC circuitry including a stepdown transformer 289 (FIG. 8) having its primary connected to 120 volt AC mains on its primary. Its secondary produces 15 volts AC on leads 270 and 271 (FIG. 8).

To supply the drive power for the switches 1,1A, 2,2A, and 3,3A, a first winding (the 15 volt winding) of a similar transformer 101 is connected to these two leads (FIG. 8). The second winding of transformer 101 produces an AC voltage sufficient to develop +130 volts DC on lead 262 when half wave rectified by diode 103 connected to a first side of the second winding and the rectified DC is smoothed by filter capacitor 102 (FIG. 8). The negative end of the filter capacitor 102 is connected at 272 to the second terminal of the second voltage winding of the transformer 101 and to the pulse output terminal 132 (FIG. 8). The pulse output terminal 132 is the common or reference potential for the circuitry of switch 1 (FIG. 8). The 15 volts AC on leads 271 and 270 supply the floating drive power for switches 2 and 3 in an identical manner (FIG. 8).

To supply a positive 20 volts for the switch circuits 47A, 47B and 47C (FIG. 8), or 15 volts for the logic circuit 43 (FIG. 9), the potential between leads 270 and 271 is also rectified by bridge rectifier diodes 291, 292, 293 and 294 to provide +20 volts (FIG. 8). Conventional +15 volt integrated circuit regulator 296 (FIG. 8) is supplied with this +20 volts and produces the regulated +15 volts also required in the pulse generator circuit 239 (FIG. 9) and logic circuitry (FIG. 9).

When control terminal 301 of the logic circuitry 43 (FIG. 9) is low, the collector of transistor 166 is high, putting a logical high on the D input of the flip-flop 153 (FIG. 9). The next time the output on lead 350 from pulse generator 138 goes high, the Q output of 153 is clocked high providing an enabling input to NAND gate 154 (FIG. 9). This brings the output of pin 11 of NAND gate 154 low and the output of pin 10 of NOR gate 155 high (FIG. 9). This enables the input 1 of NAND gate 174 and input 5 of NAND gate 169 (FIG. 9).

When the computer-implemented interval or cycle timer connected to terminal 302 is logically low, the collector of transistor 162 goes high putting a high on the D input of flip-flop 165; and if the interval timer is high, the D input of flip-flop 165 is low (FIG. 9). At the end 427A (FIG. 5) of every pulse cycle 422 (FIG. 5), pulse generator 138 (FIG. 9) produces a very short duration positive pulse at its pin 4. This turns on transistor 150 through resistor 149, bringing its collector low (FIG. 9). This brings the output of pin 10 of NAND gate 152 high producing a clock signal at pin 3 of flip-flop 165 (FIG. 9).

If the cycle timer connected to terminal 302 has changed state since the preceding clock pulse, the Q output at pin 1 and the not Q output at pin 2 of flip-flop 165 reverse their logical states (FIG. 9). Flip-flop 165 (FIG. 9) is used to ensure that the migration vector does not change in the middle of a high frequency pulse alternation cycle by synchronizing migration vector changes with the end of a high frequency pulse cycle. The network composed of diode 176, resistor 175, capacitor 177 and NOR gate 178 (FIG. 9) ensures that switch pair 2-2A (FIG. 8) turns on only after the previously on switch pair turns off. NOR gate 178 (FIG. 9) controls switch pair 2,2A (FIG. 8) through lead 181 (FIGS. 8 and 9). NOR gate 173 (FIG. 9) controls switch pair 3,3A (FIG. 8) through lead 182 (FIGS. 8 and 9).

It was later found out that it is not necessary to synchronize migration vector changes with the high frquency pulse cycle because the latter is so fast that the DNA does not move significantly during the pulse cycle. However, this synchronizing circuit was found useful for synchronizing the migration vector changes with the much slower, medium frequency field interruption pulses which are significant to the present invention.

Figure 10:
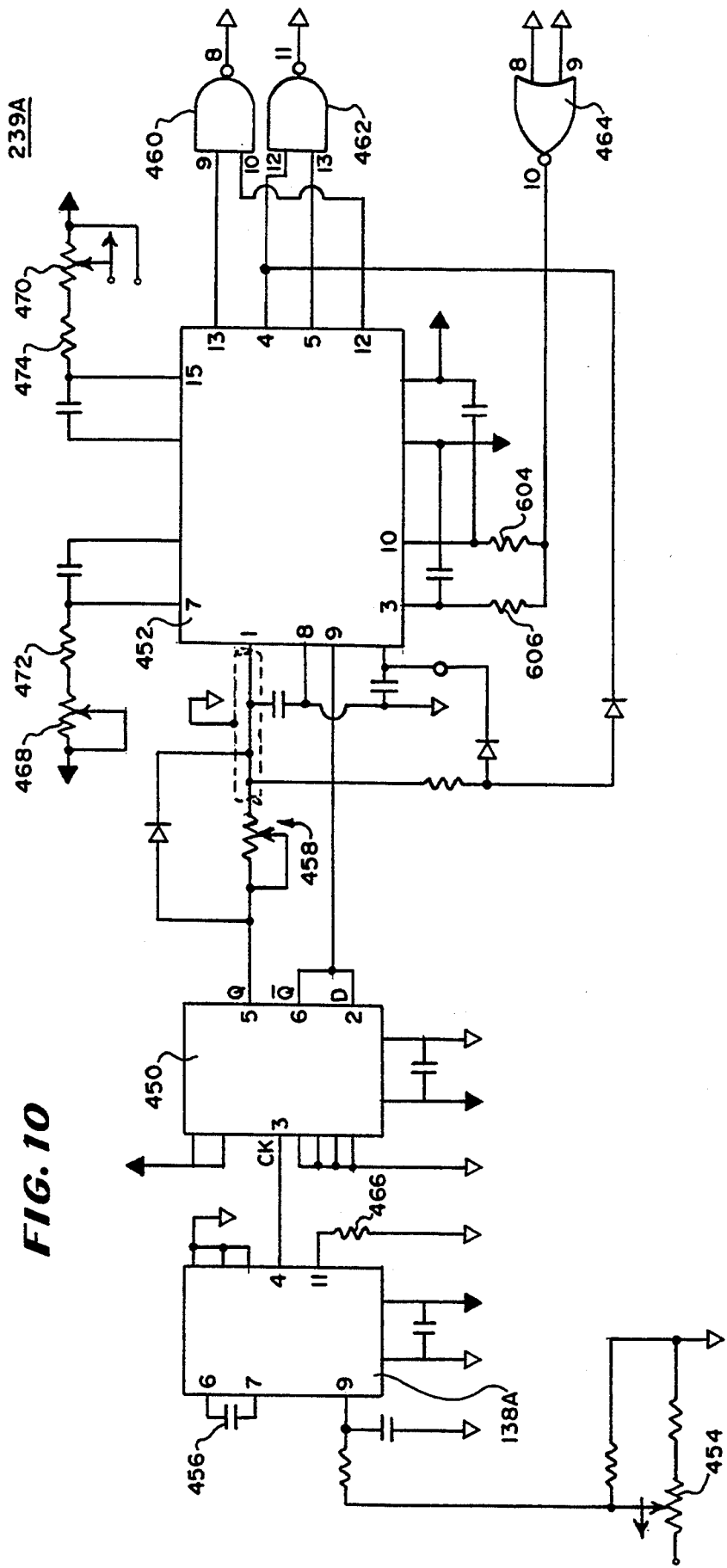
FIG. 10 is a block diagram of a switching arrangement similar to that shown in FIG. 7 except that it is adapted to produce more rapidly occurring high frequency pulses and incorporates provisions for medium frequency, short duration, cutoff of the field between the usual low frequency pulsed field electrophoresis migration direction changes.
Figure 11:
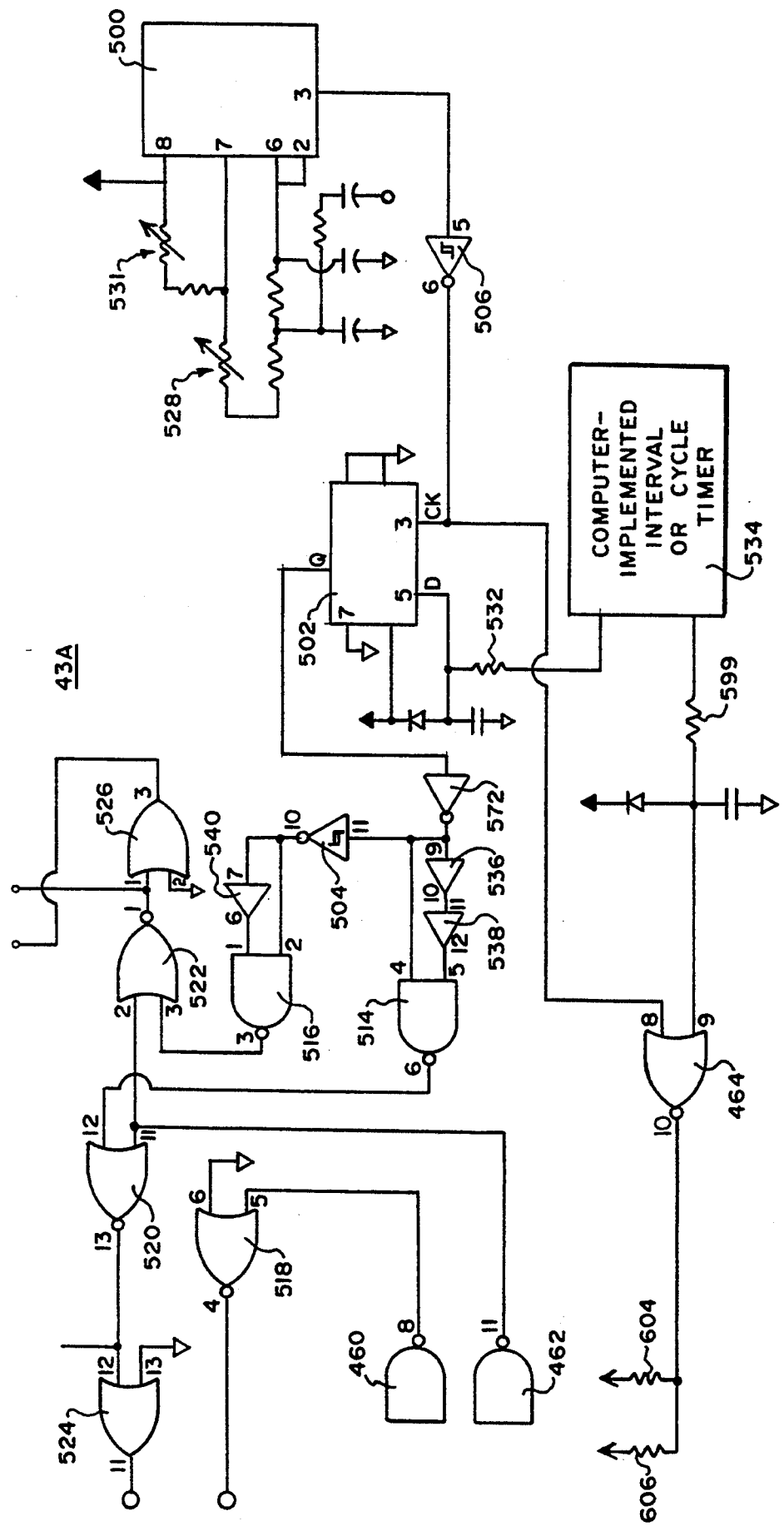
FIG. 11 is a schematic circuit diagram of a portion of the circuit of FIG. 10.
Figure 12:
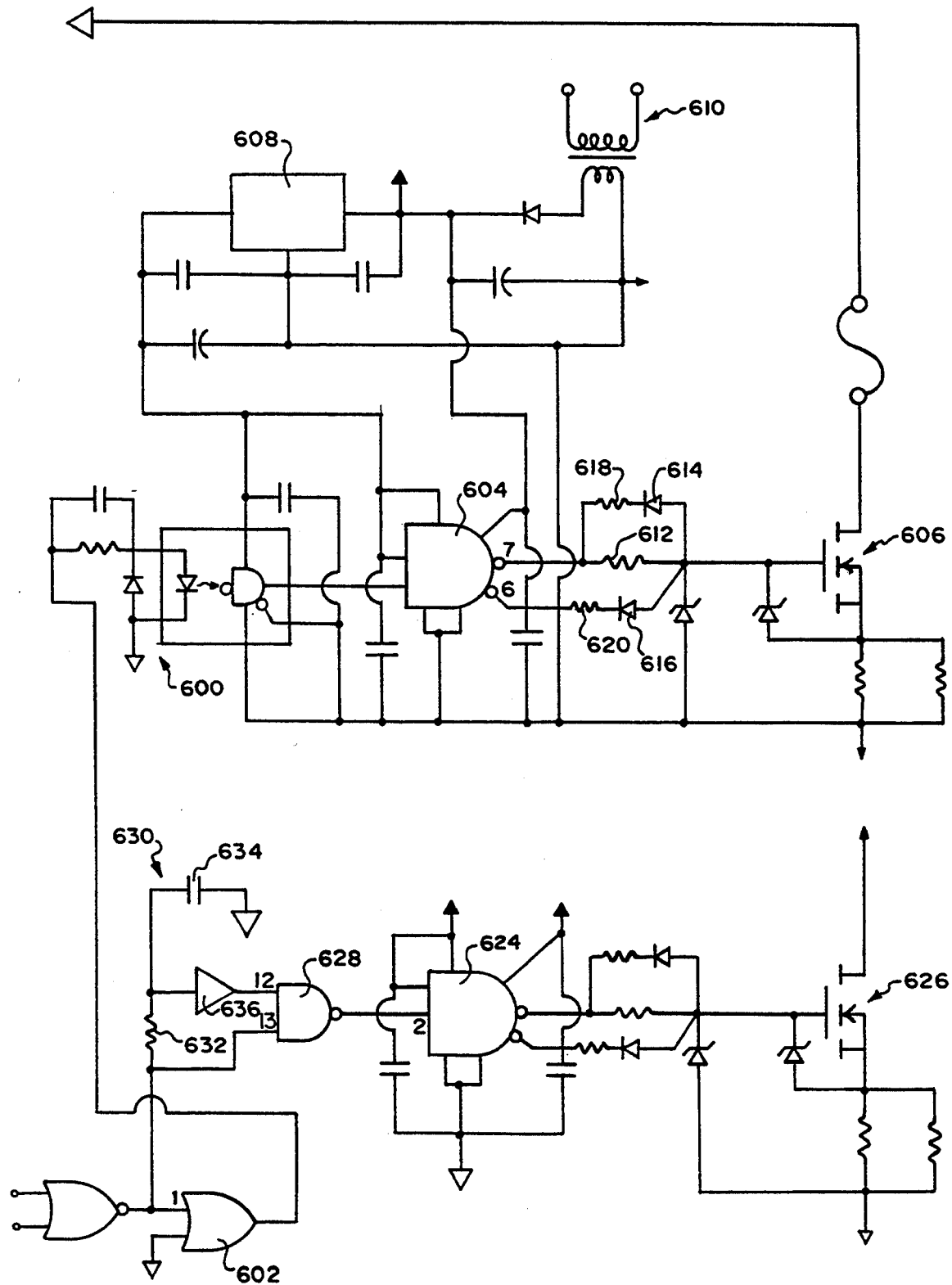
FIG. 12 is a schematic circuit diagram of a portion of the circuit of FIG. 10.

In FIGS. 10-12, there is shown another embodiment of the high frequency two-phase pulse generator along with the means for providing medium frequency field interruptions having a forward switch circuit, a right switch circuit and, a left switch circuit, each of which is shown at 47C' (FIG. 12), a logic circuit 43A (FIG. 11), and pulse generator circuit 239A (FIG. 10). With the exception of the medium frequency interruption pulse circuitry, the circuit of FIGS. 10-12 is similar to and, a refined version of, the circuit of FIGS. 8 and 9.

In FIG. 10, there is shown a schematic circuit diagram of a pulse generator circuit 239A similar in function to the pulse generator circuit 239 in FIG. 9, but in which the pulse generator 138 is replaced in pulse generator circuit 239A by voltage controlled oscillator 138A of type HC4046A, one-half of a dual D flip-flop 450 of type HC74 and dual high speed monostable multivibrator 452 of type HC423. Integrated circuit designations starting "HC" or "AC" are specific part types from the generic high speed CMOS integrated circuit families 74HCXXX or 74ACXXX respectively. The pulse generator circuit 239A includes NAND gates 460 and 462 of an integrated circuit of type HC00 and a NOR gate 464 of an integrated circuit type HC02.

In the pulse generator circuit 239A, the frequency of the voltage controlled oscillator 138A is adjusted by controlling the voltage on its pin 9 by means of the "FREQ" potentiometer 454. Its frequency range is set by the capacitor 456 connected between its pins 6 and 7 and the resistor 466 connected to its pin 11. Its output at pin 4 feeds the clock input pin 3 of flip-flop 450. The latter is connected as a divide by two circuits and is used to insure that the two inputs provided to the dual monostable multivibrator 452 at its pins 1 and 9 are exactly equal and symmetrical. The control 458 is a "SYM.-DELAY", which cooperates with capacitance on pin 8 of multivibrator 452 of type HC423, is adjusted so that the output pulses of the multivibrator 452 at pins 13 and 5 are symmetrically spaced, such as those shown at 51 and 52 in FIG. 4.

This control of the output pulses is necessary because multivibrator outputs occur after the input pulse and are therefore not symmetrical in time both before and after the input pulse. The two HC00 NAND gates 460 and 462 to the right of multivibrator 452 of type HC423 are designated NAND gate in the chip HC00 #2. The "#2" suffix merely indicates that these circuits are located in an integrated circuit chip arbitrarily designated as "#2".

The other HC00 integrated circuit chip on this schematic is designated "HC00 #1" (not shown). Each of the two HC00 chips contains four independent NAND gates (not shown), and the HC02 chip contains four independent NOR gates. The two HC00 #2 NAND gates 460 and 462 connected to the complimentary outputs at pins 13-4 and 5-12 of multivibrator 452 of type HC423 insure that their pulse outputs at pins 8 and 11 do not overlap in spite of the pulse width settings which are set by the "CROSS" potentiometer 468 and "FORWARD" potentiometer 470 connected through 2K resistors 472 and 474 to pins 7 and 15 respectively of the multivibrator 452 of type HC423.

In FIG. 11, there is shown a schematic circuit diagram of the logic circuit 43A having a medium frequency pulse generator 500, flip-flop 502, inverters 504, 506, 508, 510 and 512, NAND gate 514, and NOR gates 518, 520 and 522, and OR gates 524 and 526. The "CROSS" potentiometer 468 controls the pulse width at pins 5 and 12 of multivibrator 452 of type HC423 (FIG. 10). Therefore, through its pin 5 THE "CROSS" potentiometer 468, through pin 5 of multivibrator 452 of type HC423 controls the pin 11 output of the NAND gate 462 in the chip HC00 #2 which controls the duration of the high frequency pulses and the high frequency field in the electrophoresis tank 85 (FIG. 2) in the direction at right angles to overall long-term migration of the DNA.

The "FORWARD" potentiometer controls the pulse width at pins 13 and 4 of the multivibrator 452 of type HC423 (FIG. 10) and, through the pin 13, controls pin 8 of the NAND gate 460. The latter sets the duration of the high frequency pulses which control the high frequency field in the electrophoresis tank in the direction parallel to overall average migration direction of the DNA.

Complementary (inverted) pulses at pins 4 and 12 of multivibrator 452 of type HC423 are applied to input pins 10 and 12 of NAND gates 460 and 462 respectively to insure that simultaneous pulse outputs (pulse overlap) do not occur at the output pins 8 and 11 of NAND gates 460 and 462 respectively (FIG. 10). The output at pin 8 of the NAND gate 460 is led to pin 5 of the NOR gate 518 in HC02 which functions as an invertor and provides the control signal for the forward direction switch.

The 555 integrated circuit pulse generator 500 provides the medium-frequency field interruption pulse control signals. Interruption pulse times of 50 milliseconds through 1,200 milliseconds may be set with the "PULSE WIDTH" potentiometer 528. The repetition time of interruption pulses may be set with the "PULSE SPACING" potentiometer 531 from 1 second through 15 seconds. Of course, the maximum repetition rate is not available when using the maximum interruption pulse width.

The negative-going pulse output from pin 3 of the 555 integrated circuit pulse generator 500 is applied to pin 5 of inverter 506 where it is inverted and fed to pin 3, the clock input, of D flip-flop 502 of type 4013B. A computer-implemented repeating interval timer 534 is connected to the D input of this flip-flop through a 10K resistor 532. The flip-flop 502 synchronizes the left (and right) direction control signals from the computer-implemented interval or cycle timer 534 with the pulsing from the type 555 integrated circuit pulse generator 500. The result is that a field interruption pulse always occurs at the same time as a migration direction change. After receiving a direction change signal from the computer source of pulses 534, flip-flop 502 in dual flip-flop HC 4013B waits for the next pulse at its pin 3 before changing the state of its Q output to agree with that of its D input. Simultaneously, the pulse at pin 3 of flip-flop 502 in dual flip-flop HC 4013B is lead to pin 8 of NOR gate 464 (FIG. 10) of type HC02.

The output at pin 10 of NOR gate 464 of type HC02 then shuts off both sections of dual monostable multivibrator 452 of type HC423 by activating its NOT RESET inputs at pins 3 and 11 (FIG. 10). This shuts off its pulse outputs at pins 13 and 5, shutting off both the "FORWARD" output connected at pin 8 of NAND gate 460 in the chip HC00 #2 and the "CROSS" output at pin 11 of the NAND gate 462 in the chip HC00 #2 (FIG. 9). This shuts off the field in the tank 85. At the end of the pulse at pin 3 of the flip-flop 502 in dual flip flop HC 4013B, the field turns on again.

The migration direction output at pin 1 (Q output) of the flip-flop 502 in dual flip-flop HC 4013B is fed to pin 9 of inverter 512 of type HC14A where it is inverted and fed to pin 4 of NAND gate 514 in the chip HC00 #2. Pin 6 of NAND gate 514 is fed to pin 12 of NOR gate of type HC02 which enables NOR gate 520 of type HC02 to respond to cross direction field pulses at its pin 11 when the computer calls for migration toward the right. Pin 11 of HC14A inverter 504 is connected to pin 8 of HC14A inverter 512. Pin 10 of the HC14A inverter 504 is connected to pin 2 of NAND gate 516 in the chip HC00 #2 and this signal is inverted from the signal at pin 4 of NAND gate 514 in the chip HC00 #2.

Therefore, the output of pin 3 at the second NOR gate 526 in the HC02 enables NOR gate 522 in the HC02 at its pin 3 to respond to cross direction pulses from the high frequency pulse generator when the computer source of pulses has an output corresponding to migration in the leftwards direction. The two 4050B buffers 536 and 538 connected to the pin 5 input of NAND gate 514 in the chip HC00 #2 and the single 4050B buffer 540 connected to pin 1 of the NAND gate 516 in the chip HC00 #2 provide a time delay that insures that the control circuit will not attempt to instantaneously turn on both the rightwards and leftwards migration outputs for a short instant between migration changes from rightwards to leftwards or leftwards to rightwards.

In FIG. 12, there is shown a schematic circuit diagram of one of three dual switching circuits 47A', 47B' and 47C'. The three identical dual switching circuits are similar to that in FIG. 7 and operate in a similar manner.

Differences in the switches 47A-47C and 47A'-47C' are: (1) the optoisolator 600 in each isolated switch is an HCPL2411 driven by an AC42 integrated circuit 602 instead of a 6N136 optoisolator driven by a 2N3904 transistor; (2) a SN75372 integrated circuit 604 MOSFET driver is used to drive the base of the MTP1N60 transistor 606 instead of a 2N3904 transistor; (3) integrated circuit 7805 voltage regulator 608 is used instead of a 5.6 volt zener diode to supply power to the low voltage circuitry; and (4) the isolating power transformer 610 used is a 120 to 12 volt AC Stancor SW-212, chosen for its low primary to secondary capacitance.

Many other small, bobbin wound transformers would be equally satisfactory in this respect. However, the transformer 610 should be mounted so that its core has low capacitance to all other circuit points, including the circuit common. The SN75372 driver 604 turns on the MOSFET power transistor 606 through a 47 ohm resistor 612.

The SN75372 integrated circuit is a dual device. In order that the turn off of the transistor 606 be faster than the turn on of the transistor 606, additional turn off paths of series connected 1N4150 diodes 614 and 616 and 8.2 ohm resistors 618 and 620 are connected to the gate of the power field effect transistor 606 and each of the dual outputs at pin 6 and pin 7 of the SN75372 driver 604. Its dual input terminal is pin 2. The MOSFET turn on time is about 50 nanoseconds and the turn off time is about 25 nanoseconds. This helps prevent more than one pair of the dual switches from being on at one time.

The non-isolated power field effect transistor 626 is driven through the similar SN75372 drive circuit 624 which in turn is driven at its pin 2 by an HC00 #1 NAND gate 628. The HC00 #1 NAND gate 628 has two inputs, one of which at 13 is connected directly to the pulse control signal from the control circuitry and the other through a delay circuit 630 consisting of a 680 ohm resistor 632, 47 picofarad capacitor 634 and the relatively slow propagation time of a 4050B buffer 636. This delay circuit of approximately 90 nanoseconds ensures that the non-isolated power MOSFET in each dual switch turns on after the isolated MOSFET turns on.

This delay circuit has no effect during turnoff so the non-isolated power MOSFET 626 turns off before the isolated one, because of the modest (Ca. 55 nanoseconds) propagation delay of the HCPL2411 optoisolator 600 in the isolated MOSFET 606 single path. It helps prevent more than one pair of the dual switches 47A'-47C' from being on at one time. This dual switching circuit 47C' provides the very fast and precise timing accuracy and stability necessary for switching up to 500 volts at a frequency of up to 1 megahertz.

Figure 13:
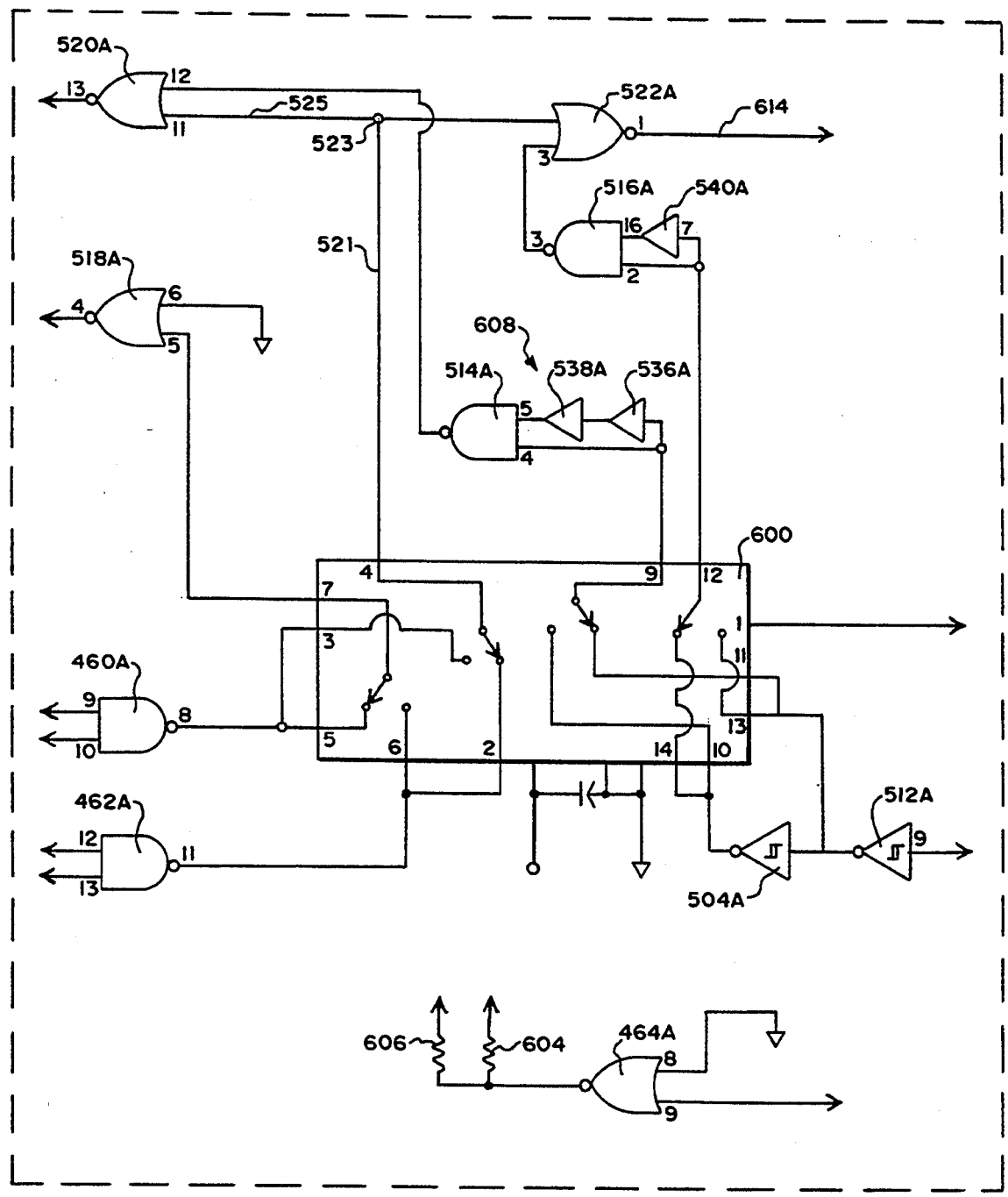
FIG. 13 is a schematic drawing of a modification which may be made to the schematic of FIG. 10 to provide medium frequency, short duration, perpendicular change in field direction instead of short duration field cutoff.

To provide for field interruptions that are short-time perpendicular field direction changes instead of short-time field cutoffs, the 4-pole, double throw switching arrangement shown in FIG. 13 is added to the circuit of FIGS. 10–12. In FIGS. 10–12, the field is cut off during interruptions by resetting the dual monostable multivibrator 452 of type HC423 (FIG. 10) by carrying the interruption pulse from pin 3 of the synchronizing flip-flop 502 in dual flip-flop HC 4013B to the pin 8 input of NOR gate in the HC02 whose output is connected to the pin 3 and pin 11 NOT RESET inputs of monostable multivibrator 452 of type HC423.

There is shown in FIG. 13 a modification of the schematic of FIG. 11 to provide medium frequency, short duration, perpendicular change in field direction having: (1) an AC157 quadruple 2-input multiplexer integrated circuit 600; (2) a run/stop control including a type HC02 NOR gate 464A and 330 ohm resistors 604 and 606; (3) a right pulse train control including an inverter 512A in the HC14A, an inverter 504A, the multiplexer 600, 4050B amplifiers 536A and 538B and NAND gate 514A in the chip HC00 #2 forming a time delay 608, a conductor 521 and NOR gate 520A in the HC02; (4) a clock pulse train control having a NAND gate 462A in the chip HC00 #2 and a conductor 521; (5) a left pulse train control having inverters 512A and 504A connected to the multiplexer 600, 4050B amplifier 540A, NAND gate 516A in the chip HC00 #2 and NOR gate 522A in the HC02; (6) a forward pulse train control having NAND gate 462A of the chip HC00 #2 and NOR gate 518A in the HC02; and (7) an interruption control having a connection at pin 1 of the integrated circuit 600 with pin 3 of flip-flop 502 in dual flip-flop HC4013B (FIG. 11).

A run/stop control is used to start and stop the multivibrator integrated circuit 452 (FIG. 10). Typically, this control is used to turn on the electrophoresis voltage at the start of a separation run and turn off the voltages at the end of a run. The inverter 510 (FIGS. 1 and 11) has its input connected through resistor 599 to receive an on/off signal voltage originating from the computer-implemented interval timer 534 (FIG. 11). The resistor 604 is connected to NOT RESET pin 10 of dual high speed monostable multivibrator 452 of type HC423 and resistor 606 is connected to NOT RESET pin 3 of monostable multivibrator 452. When the on/off signal voltage from the computer is logically high, this resets both the FORWARD and CROSS sections of the multivibrator 452, shutting off the high frequency pulses to the electrophoresis tank 85 (FIG. 2). When this signal voltage is logically low, this turns on the high frequency pulses to the tank 85.

The right pulse train control is used to control the right pulses. To send a pulse to right dual switching circuit 47B' (corresponding the left dual switching circuit 47C' of FIG. 12), a pulse is received by pin 9 of inverter 512A through pin 1 of flip-flop 502 in dual flip-flop HC 4013B (FIG. 11). The pulse is inverted and then transmitted to inverter 504A which returns the pulse to its original voltage level. The pulse is then received by input pin 10 of the integrated circuit 600 which is connected to its output pin 9 during interruptions and its pin 11 is connected to pin 9 and its pin 14 is connected to pin 12 between interruptions. The output pin 9 is connected to NAND gate 514A directly at its pin 4 and indirectly through amplifiers 536A and 538A to pin 5 of the NAND gate 514A. This causes a time delay of the pulse to pin 12 of NOR gate 520A. The output pin 13 of NOR gate 520A is connected to an AC32 OR gate in the right dual switching circuit 47B' (not shown) corresponding to the AC32 OR gate 602 of the left dual switching circuit 47C' (FIG. 12).

Output pins 13 and 12 of the dual high speed monostable multivibrator 452 of type HC423 (FIG. 10) are connected to the input pins 9 and 10 of the NAND gate 460A of the HC00 #2 chip and the output pin 8 of the NAND gate 460A is connected to pins 3 and 5 of the integrated circuit 600. During interruptions, pin 3 of the integrated circuit 600 is connected to pin 4 and between interruptions, pin 5 of the integrated circuit 600 is connected to pin 7. To send high frequency pulses to the right dual switching circuit 47B', pin 4 of the integrated circuit 600 is connected through conductor 521 to conductor 525 at 523, which conductor 525 is connected to NOR gate 520A in the HC02 at its pin 11.

The left pulse train control controls the pulses to the left dual switching circuit. To send pulses to left dual switching circuit 47C' (FIG. 12), a voltage level is transmitted to pins 11 and 13 of the integrated circuit 600 through the inverter 512A by the flip-flop 502 (FIG. 11). During interruptions, pin 13 of the integrated circuit 600 is connected to pin 12 and in turn is received by: (1) pin 7 of the amplifier 540A before being received by NAND gate 516A at its pin 16; and (2) NAND gate 516A at its pin 2. Output pin 3 of NAND gate 516A is connected to pin 3 of NOR gate 522A and output pin 1 of NOR gate 522A is connected to pin 1 of AC32 OR gate 602 (FIG. 12) and pin 13 of NAND gate 628 of the chip HC00 #1 (FIG. 12).

The forward pulse train control controls the pulses to the forward dual switching circuit 47A'. Pulses are transmitted through pins 13 and 12 of the monostable multivibrator 452 to pins 9 and 10 of NAND gate 460A. Output pin 8 of NAND gate 460A is connected to pins 5 and 3 of the integrated circuit 600. Between interruptions pin 5 of the integrated circuit 600 is connected to its pin 7. During interruptions, pin 6 of the integrated circuit 600 is connected to its pin 7 which is then connected to pin 5 of NOR gate 518A. Output pin 4 of NOR gate 518A is connected to pin 5 of an AC32 OR gate and pin 5 of a NAND gate of the chip HC00 #1 in the forward dual switching circuit 47A' (not shown) corresponding to the AC32 OR gate 602 and NAND gate 628 of the left dual switching circuit 47C' (FIG. 12).

The interruption control is used to enable or disable the field interruption pulses from the type 555 integrated circuit pulse generator 500 (FIG. 11). Because there is no connection between pin 3 of flip-flop 502 in dual flip-flop HC 4013B (FIG. 11) and pin 8 of NOR gate 464A in the HC02 in this embodiment, and pin 8 of NOR gate 464A in the HC02 is grounded, the interruption pulses do not cut off the electric field. Instead the interruption pulses are led from pin 3 of flip-flop 502 (FIG. 11) in dual flip-flop HC4013B to pin 1, the selection input, of the AC157 quadruple 2-input multiplexer integrated circuit 600 which is connected as a 4-pole double throw switch whose switch position is set by the logic voltage on pin 1 of the integrated circuit.

A 4-pole double throw switch is used because it can produce perpendicular direction changes. The following trigonometric identity of equation 3 supports this.

In equation 3, "A" represents the time duration of one high frequency pulse crossways to the direction of overall average migration and B represents the time duration of one high frequency pulse in the direction parallel to that of the overall average migration of the DNA. Thus, the direction of the field can be made to shift 90 degrees by using the normally "forward" pulses from pin 8 of NAND gate 460A in the chip HC00 #2 to control the field in the right or left (cross) direction; and to use the normally "cross" pulses from pin 11 of the NAND gate 462A in the chip HC00 #2 to control the field in the forward direction FIG. 10). The minus sign in the argument on the right side of the equation means that the right and left voltage pulse outputs to the tank 85 (FIG. 2) must also be reversed. This is accomplished by reversing the pin 2 and pin 4 inputs of two of the NAND gates 516A and 514A in the chip HC00 #2. A 4-pole double throw switch can easily be used to reverse two independent circuits, since a 2-pole double throw switch can be used to reverse one independent circuit.

Between interruptions, pin 1 of the AC157 integrated circuit 600 is low. At this time, its pin 2 is connected to pin 4, pin 5 is connected to pin 7, pin 11 is connected to pin 9 and pin 14 is connected to pin 12. These connections provide the same circuit path as in FIGS. 10–12. During interruptions, pin 1 of AC157 is high. In this case, pin 3 is connected to pin 4, pin 6 is connected to pin 7, pin 13 is connected to pin 12 and pin 10 is connected to pin 9. This change constitutes reversals in accordance with the trigonometric identity above and therefore the field direction in the tank 85 changes perpendicularly in a direction more oriented than not toward the direction of the overal 1 average direction of DNA migration.

The interruptions need not necessarily be sharp or pulse-like. Perturbations that are either sharp or gradual can accomplish the required functions.

The optimum pulse durations for perpendicular field interruptions are shorter than the pulse directions for field-cutoff interruptions or the power supply connected to the circuit of FIGS. 8 or 12 should be turned down to a lower voltage during the interruption pulses if perpendicular interruptions are used. This is necessary so that, while there is enough time for relaxation of the counterion sheath during such interruptions, there is not sufficient time for a significant length of DNA to change direction.

The buffer in tank 85 (FIG. 2) should be kept well circulated to prevent pH changes at the electrodes from causing crooked migrating lanes. The preferred method of buffer circulation is to continuously stir the tank 85 (FIG. 2) with a pair of rotating paddles immersed in the buffer and whose path describes a single, horizontal, circle in the space between the gel 90 and the electrodes on the inside periphery of the tank 85 (FIG. 2). A speed of 15 to 20 rpm is adequate. To prevent dislocation of the gel, it is allowed to remain in situ on its glass casting plate after pouring. The glass plate and the attached gel is then fit between plastic locating strips glued onto the inside bottom of the tank 85 (FIG. 2). The space defined by these strips corresponds to the dimensions of the glass plate, so the plate is held in place.

EXAMPLES

The apparatus used was the 2-phase high frequency vector-generation pulsed gel electrophoresis apparatus of the type described above. It has been found that increasing the frequency of the high frequency pulses to 400 kilohertz, provides improved performance with ordinary pulsed gel electrophoresis. The frequency of 400 kilohertz may be an optimum as it appears to provide slightly better performance than 800 kilohertz and 400 kilohertz at a duty factor of 75 percent was used as a 2-phase high frequency vector generation frequency for pulsed gel electrophoresis incorporating additional medium frequency interruptions.

A pulsed gel electrophoresis switching angle of 120 degrees was used. Experiments were made with *S. pombe* chromosonal DNA; starting with 30 minute switching times between changes in the angle of migration, a field strength of 1.5 volts per centimeter, and a running time of 70 hours. In the first experiments, 10 millisecond medium-frequency field cutoff interruptions were used at a repetition rate of once per second. There was no marked improvement in the separation.

The second experiment used 100 millisecond cutoff interruptions every five seconds. Not only did the bands become sharper in the second case but the velocity of migration actually increased in spite of a slight decrease in the average field due to the 2 percent off-time of the interruptions. This is attributed to decreased bunching. Later experiments established that good *S. pombe* separations can be made in well under 20 hours merely by raising the field to 3.1 volts per centimeter, changing the interruption timing to 160 millisecond interruptions every 2.3 seconds and the switching time to 45 minutes per angle change. Comparable results were obtained with chromosomal DNA from the fungus *Colletotrichum trifolii*. All separations were made with the $0.5 \times$ TBE buffer commonly used for ordinary pulsed field gel electrophoresis.

Some of the processes of this invention can be performed using more general apparatuses such as the PACE system described in Birren, B.W., Lai, E., Clark, S.M., Hood, L. and Simon, M.I. (1988), "Optimized Conditions for Pulsed Field Gel Electrophoretic Separations of DNA," *Nucleic Acids Res.* 16:7563–7582 and in Clark, S.M., Lai, E., Birren, B.W. and Hood, L. (1988), "A Novel Instrument for Separating Large DNA Molecules with Pulsed Homogeneous Electric Fields," *Science* 241:1203–1205. However, simpler less expensive equipment can be used. For example, it is only necessary to have two pairs of electrode sets on four sides of the gel and simple controls for pulse frequencies and polarity changes rather than a computer which varies values for many independent electrodes and the complicating circuitry. The electrodes are open circuited by a diode transistor combination when not supplying pulses rather than being clamped to a fixed potential and thus sneak paths are avoided in relatively inexpensive circuit adapted to perform the method of this application.

As can be under s rood f tom the above description, the electrophoresis apparatus of this invention has several advantages, such as for example: (1) it is relatively uncomplex and inexpensive; (2) it is able to separate large DNA molecules; (3) it does not result in bent or curved lanes of travel of the DNA; (4) it is versatile in handling different sizes of DNA strands; and (5) its uncomplex nature makes it easy to use. The internal electronic design which provides for this versatility does not require an external computer or a matrix of matched or expensive circuits, each of which must be independently adjusted or programmed. Thus, it is easier to use and its cost is much lower than the PACE system.

Although a preferred embodiment of the invention is described with some particularity, many modifications and variations of the preferred embodiment are possible without deviating from the invention. Therefore, it is to be understood that within the scope of the appended claims the invention may be practiced other than as specifically described.

What is claimed is:

1. A method of pulsed field electrophoresis of substances comprising the steps of:
   changing the time average direction of an electric field within an electrophoresis separating unit at a first frequency; and
   changing the electric field in another manner at a second frequency at least twice as high as the said first frequency; the step of changing the electric field in the said other manner including the step of changing the magnitude of the electric field.

2. A method of pulsed field electrophoresis comprising the steps of:
   changing the time average direction of an electric field within an electrophoresis separating unit at a first frequency; and
   changing the electric field in another manner at a second frequency at least twice as high as the said first frequency;
   the step of changing the time average direction of an electric field including the step of changing the angle of the field to impart a zigzag path to DNA molecules being separated; wherein the step of changing the electric field in the said other manner includes the step of changing the magnitude of the electric field.

3. A method of pulsed field electrophoresis comprising the steps of:
   changing the time average direction of an electric field within an electrophoresis separating unit of a first frequency, wherein the first frequency has a period greater than 20 seconds; and changing the electric field in another manner of a second frequency at least twice as high as the first frequency,
   the step of changing the electric field in another manner including the step of applying perturbating interruption pulses, the perturbating interruptions pulse having pulse widths not exceeding one-half of the period of the repetition of the perturbating interruption pulses.

4. A method according to claim 3 wherein there are at least two perturbations during each direction or half cycle of the first frequency.

5. A method for separation of DNA according to claim 4 in which the magnitude of the field and the characteristic of the perturbation are selected to avoid bunching across the probable length of the first segment of DNA to its first direction change wherein the direction change is in the range of substantially 90 degrees to a value greater than 90 degrees.

6. A method for separating large DNA by pulsed field gel electrophoresis comprising the steps of:
   applying a first pulsed electric field parallel to the direction of overall DNA migration with first pulse durations and a first pulse frequency for a first pulsed field duration of at least 20 seconds;
   applying a second pulsed electric field at an angle perpendicular to the direction of overall migration, wherein said second pulsed electric field starts with a first polarity and undergoes a first continuous time period of rapid pulses having pulse durations occurring between different ones of said first pulsed field durations at a frequency equal to said first pulse frequency multiplied by an integer or a reciprocal of an integer; and
   repeating the sequence, and at each repetition, alternating the frequencies of the first and second electric field pulses for an extended period of time; wherein said first and second pulsed electric fields have a frequency selected between 10 hertz and 1 megahertz and have pulses which alternate with each other.

7. Apparatus for pulsed field electrophoresis comprising:
   means for changing the time average direction of an electric field within an electrophoresis separating unit at a first frequency; and
   means for changing the electric field in another manner at a second frequency at least twice as high as the said first frequency; wherein said means for changing the electric field at a second frequency includes means for changing the magnitude of the electric field.

8. Apparatus for pulsed field electrophoresis comprising:
   means for changing the time average direction of an electric field within an electrophoresis separating unit at a first frequency; and
   means for changing the electric field in another manner at a second frequency at least twice as high as the said first frequency; wherein said means for changing the direction of an electric field includes means for changing the angle of the field to impart a zigzag path to DNA molecules being separated; and wherein the means for changing the electric field at a second frequency includes means for changing the magnitude of the electric field.

9. Apparatus for separating large DNA by pulsed field gel electrophoresis comprising:
   means for applying a first pulsed electric field parallel to the direction of overall DNA migration with first pulse durations and a first pulse frequency for a first pulsed field duration of at least 20 seconds;
   means for applying a second pulsed electric field at an angle perpendicular to the direction of overall migration, wherein said second pulsed electric field starts with a first polarity and undergoes a first continuous time period of rapid pulses having pulse durations occurring between different ones of said first pulsed field durations at a frequency equal to said first pulse frequency multiplied by an integer or a reciprocal of an integer; and
   means for repeating the sequence, each time alternating the frequencies of the first and second electric field pulses for an extended period of time; wherein said first and second pulsed electric fields have a frequency selected between 10 hertz and 1 megahertz and have pulses which alternate with each other.

10. A method of pulsed field electrophoresis of large DNA above two megabases, comprising the steps of:
    changing the time average direction of an electric field within an electrophoresis separating unit at a first frequency having a period of at least twenty seconds; and
    changing the electric field in another manner at a second frequency at least twice as high as the said first frequency, wherein the step of changing the electric field in another manner includes pertubations of the electric field, each of which has a time duration shorter than one-tenth second.

11. Apparatus for pulsed field electrophoresis comprising:

means for changing the time average direction of an electric field within an electrophoresis separating unit at a first frequency having a period of at least twenty seconds; and means for changing the electric field at a second frequency at least twice as high as the said first frequency with perturbations each of which has a time duration shorter than one-tenth second.

* * * * *